(12) United States Patent (10) Patent No.: US 8,772,272 B2
Freyne et al. (45) Date of Patent: Jul. 8, 2014

(54) PYRIDO-AND PYRIMIDOPYRIMIDINE DERIVATIVES AS ANTI-PROLIFERATIVE AGENTS

(75) Inventors: Eddy Jean Edgard Freyne, Rumst (BE); Marc Willems, Vosselaar (BE); Pierre Henri Storck, Rouen (FR); Virginie Sophie Poncelet, Le Manoir sur Seine (FR); Kristof Van Emelen, Sint-Niklaas (BE); Peter Jacobus Johnnes Antonius Buijnsters, Breda (NL); Werner Constant Johan Embrechts, Oud-Turnhout (BE); Timothy Pietro Suren Perera, Geel (BE)

(73) Assignee: Janssen Pharmaceutica NV, Beerse (BG)

( * ) Notice: Subject to any disclaimer, the term of this patent is extended or adjusted under 35 U.S.C. 154(b) by 986 days.

(21) Appl. No.: 12/724,203

(22) Filed: Mar. 15, 2010

(65) Prior Publication Data

US 2010/0173913 A1 Jul. 8, 2010

Related U.S. Application Data

(62) Division of application No. 10/596,512, filed as application No. PCT/EP2004/053501 on Dec. 15, 2004, now Pat. No. 7,799,772.

(30) Foreign Application Priority Data

Dec. 18, 2003 (WO) ..................... PCT/EP03/51058
Dec. 18, 2003 (WO) ..................... PCT/EP03/51062

(51) Int. Cl.
*A61K 31/33* (2006.01)
*A61K 31/519* (2006.01)
*C07D 487/00* (2006.01)
*C07D 487/18* (2006.01)

(52) U.S. Cl.
USPC ............ 514/183; 540/471; 540/472; 544/256

(58) Field of Classification Search
None
See application file for complete search history.

(56) References Cited

U.S. PATENT DOCUMENTS

| | | | |
|---|---|---|---|
| 4,067,726 A | 1/1978 | Sasse et al. | |
| 4,160,836 A | 7/1979 | Vandenberk et al. | |
| 4,442,278 A | 4/1984 | Giants | |
| 5,679,683 A | 10/1997 | Bridges et al. | |
| 5,721,237 A | 2/1998 | Myers et al. | |
| 5,770,599 A | 6/1998 | Gibson | |
| 5,821,240 A | 10/1998 | Himmelsbach et al. | |
| 6,002,008 A | 12/1999 | Wissner et al. | |
| 6,265,410 B1 | 7/2001 | Bridges et al. | |
| 6,288,082 B1 | 9/2001 | Wissner et al. | |
| 6,344,459 B1 | 2/2002 | Bridges et al. | |
| 6,414,148 B1 | 7/2002 | Thomas et al. | |
| 6,521,620 B1 | 2/2003 | Bridges et al. | |
| 6,602,863 B1 | 8/2003 | Bridges et al. | |
| 6,794,395 B1 | 9/2004 | Roth et al. | |
| 7,067,507 B2 | 6/2006 | Pulley et al. | |
| 7,312,225 B2 | 12/2007 | Luecking et al. | |
| 7,648,975 B2 | 1/2010 | Freyne et al. | |
| 7,655,642 B2 | 2/2010 | Freyne et al. | |
| 7,799,772 B2 | 9/2010 | Freyne et al. | |
| RE42,353 E | 5/2011 | Thomas et al. | |
| 2002/0173646 A1 | 11/2002 | Thomas et al. | |

(Continued)

FOREIGN PATENT DOCUMENTS

GB    807899 A    1/1959
GB    1465451 A   2/1977

(Continued)

OTHER PUBLICATIONS

Rewcastle, Journal of Medicinal Chemistry, 1996, 39, 1823-26.*

(Continued)

*Primary Examiner* — Noble Jarrell

(57) ABSTRACT

The present invention concerns the compounds of formula (I)

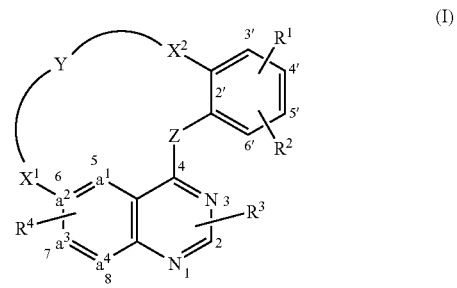

the N-oxide forms, the pharmaceutically acceptable addition salts and the stereochemically isomeric forms thereof, wherein
$a^1$-$a^2$=$a^3$-$a^4$ represents a divalent radical selected from N—CH=CH—CH, N—CH=N—CH or CH—CH=N—CH;
Z represents NH; Y represents —$C_{3-9}$alkyl-, —$C_{1-5}$alkyl-N$R^{13}$—$C_{1-5}$alkyl-, —$C_{1-6}$alkyl-NH—CO— or —CO—NH—$C_{1-6}$alkyl-;
$X^1$ represents —O— or —N$R^{11}$—; $X^2$ represents —$C_{1-2}$alkyl-, —O—$C_{1-2}$alkyl, —O— or —O—$CH_2$—;
$R^1$ represents hydrogen or halo;
$R^2$ represents hydrogen, cyano, halo, hydroxycarbonyl-, $C_{1-4}$alkyloxycarbonyl-, $Het^{16}$-carbonyl- or $Ar^5$; $R^3$ represents hydrogen;
$R^4$ represents hydroxy, $C_{1-4}$alkyloxy, $Ar^4$—$C_{1-4}$alkyloxy or $R^4$ represents $C_{1-4}$alkyloxy substituted with one or where possible two or more substituents selected from $C_{1-4}$alkyloxy- or $Het^2$-;
$R^{11}$ represents hydrogen;
$R^{12}$ represents hydrogen, $C_{1-4}$alkyl- or $C_{1-4}$alkyl-oxy-carbonyl-;
$R^{13}$ represents $Het^{14}$-$C_{1-4}$alkyl, in particular morpholinyl-$C_{1-4}$alkyl;
$Het^2$ represents a heterocycle selected from morpholinyl or piperidinyl optionally substituted with $C_{1-4}$alkyl-, preferably methyl;
$Het^{14}$ represents morpholinyl;
$Het^{16}$ represents a heterocycle selected from morpholinyl or pyrrolidinyl;
$Ar^4$ represents phenyl; $Ar^5$ represents phenyl optionally substituted with cyano.

3 Claims, No Drawings

(56) References Cited

U.S. PATENT DOCUMENTS

| | | |
|---|---|---|
| 2003/0087908 A1 | 5/2003 | Geuns-Meyer et al. |
| 2003/0186987 A1 | 10/2003 | Bridges et al. |
| 2004/0048880 A1 | 3/2004 | Himmelsbach et al. |
| 2004/0116388 A1 | 6/2004 | Armistead et al. |
| 2005/0009867 A1 | 1/2005 | Hennequin |
| 2005/0250797 A1 | 11/2005 | Hennequin et al. |
| 2007/0078132 A1 | 4/2007 | Freyne et al. |
| 2008/0219975 A1 | 9/2008 | Perera et al. |
| 2009/0075999 A1 | 3/2009 | Blanchard et al. |
| 2010/0029627 A1 | 2/2010 | Papanikos et al. |
| 2010/0069424 A1 | 3/2010 | Freyne et al. |
| 2010/0105668 A1 | 4/2010 | Freyne et al. |
| 2010/0152174 A1 | 6/2010 | Freyne et al. |
| 2010/0160310 A1 | 6/2010 | Freyne et al. |
| 2010/0190786 A1 | 7/2010 | Diels et al. |
| 2010/0204197 A1 | 8/2010 | Diels et al. |
| 2010/0222574 A1 | 9/2010 | Rombouts et al. |
| 2011/0009404 A1 | 1/2011 | Buijnsters et al. |

FOREIGN PATENT DOCUMENTS

| | | |
|---|---|---|
| GB | 1542514 A | 3/1979 |
| WO | WO-95/19774 A1 | 7/1995 |
| WO | WO-95/19970 A1 | 7/1995 |
| WO | WO-96/07657 A1 | 3/1996 |
| WO | WO-96/09294 A1 | 3/1996 |
| WO | WO-96/33980 A1 | 10/1996 |
| WO | WO-96/39145 A1 | 12/1996 |
| WO | WO-97/32880 A1 | 9/1997 |
| WO | WO-97/38983 A1 | 10/1997 |
| WO | WO-98/13354 A1 | 4/1998 |
| WO | WO-98/43960 A1 | 10/1998 |
| WO | WO-99/33792 A2 | 7/1999 |
| WO | WO-99/33793 A2 | 7/1999 |
| WO | WO-99/33795 A1 | 7/1999 |
| WO | WO-99/33815 A1 | 7/1999 |
| WO | WO-00/18761 A1 | 4/2000 |
| WO | WO-00/55159 A2 | 9/2000 |
| WO | WO-01/16130 A1 | 3/2001 |
| WO | WO-02/20479 A1 | 3/2002 |
| WO | WO-02/083654 A1 | 10/2002 |
| WO | WO-03/072062 A2 | 9/2003 |
| WO | WO-03/082290 A1 | 10/2003 |
| WO | WO-2004/004732 A1 | 1/2004 |
| WO | WO-2004/009562 A1 | 1/2004 |
| WO | WO-2004/014899 A1 | 2/2004 |
| WO | WO-2004/026829 A2 | 4/2004 |
| WO | WO-2004/026881 A1 | 4/2004 |
| WO | WO-2004/037814 A1 | 5/2004 |
| WO | WO-2004/043936 A1 | 5/2004 |
| WO | WO-2004/074224 A1 | 9/2004 |
| WO | WO-2004/078682 A2 | 9/2004 |
| WO | WO-2004/105765 A1 | 12/2004 |
| WO | WO-2005/058318 A1 | 6/2005 |
| WO | WO-2005/058913 A1 | 6/2005 |
| WO | WO-2006/061415 A1 | 6/2006 |
| WO | WO-2006/061417 A2 | 6/2006 |
| WO | WO-2007/003525 A2 | 1/2007 |
| WO | WO-2007/058267 A1 | 5/2007 |
| WO | WO-2007/058627 A1 | 5/2007 |
| WO | WO-2007/058628 A1 | 5/2007 |
| WO | WO-2008/006884 A2 | 1/2008 |
| WO | WO-2008/049902 A2 | 5/2008 |
| WO | WO-2008/155421 A2 | 12/2008 |
| WO | WO-2009/016132 A1 | 2/2009 |
| WO | WO-2009/112439 A1 | 9/2009 |

OTHER PUBLICATIONS

In the U.S. Patent and Trademark Office U.S. Appl. No. 10/558,007 Non-Final Office Action dated Apr. 28, 2008, 5 pages.
In the U.S. Patent and Trademark Office U.S. Appl. No. 10/558,007 Non-Final Office Action dated Nov. 25, 2008, 5 pages.
In the U.S. Patent and Trademark Office U.S. Appl. No. 10/596,509 Non-Final Office Action dated Nov. 26, 2008, 6 pages.
In the U.S. Patent and Trademark Office U.S. Appl. No. 11/720,681 Non-Final Office Action dated Mar. 3, 2011, 6 pages.
In the U.S. Patent and Trademark Office U.S. Appl. No. 11/720,681 Non-Final Office Action dated Sep. 14, 2010, 7 pages.
In the U.S. Patent and Trademark Office U.S. Appl. No. 11/875,288 Final Office Action dated Sep. 24, 2009, 2009, 8 pages.
In the U.S. Patent and Trademark Office U.S. Appl. No. 11/875,288 Non-Final Office Action dated Apr. 15, 2009, 8 pages.
In the U.S. Patent and Trademark Office U.S. Appl. No. 11/993,237 Final Office Action dated Jul. 21, 2011, 5 pages.
In the U.S. Patent and Trademark Office U.S. Appl. No. 11/993,237 Non-Final Office Action dated Dec. 10, 2010, 7 pages.
In the U.S. Patent and Trademark Office U.S. Appl. No. 12/373,404 Final Office Action dated Jun. 28, 2011, 47 pages.
In the U.S. Patent and Trademark Office U.S. Appl. No. 12/373,404 Non-Final Office Action dated Oct. 27, 2010, 12 pages.
In the U.S. Patent and Trademark Office U.S. Appl. No. 12/624,637 Non-Final Office Action dated Feb. 2, 2012, 5 pages.
In the U.S. Patent and Trademark Office U.S. Appl. No. 12/670,670 Final Office Action dated Mar. 9, 2012, 5 pages.
In the U.S. Patent and Trademark Office U.S. Appl. No. 12/670,670 Non-Final Office Action dated Nov. 9, 201, 10 pages.
In the U.S. Patent and Trademark Office U.S. Appl. No. 11/720,693 Non-Final Office Action dated Jul. 21, 2010, 6 pages.
In the U.S. Patent and Trademark Office U.S. Appl. No. 11/720,693 Final Office Action dated Apr. 11, 2011, 5 pages.
Abe et al., "Fyn kinases-mediated phosphorylation of NMDA receptor NR2B subunit at Tyr1472 is essential for maintenance of neuropathic pain" *Eur J Neurosci*, 2005; 22:1445-1454.
Anderson, "The process of structure-based drug design", *Chem Biol.*, 2003; 10:787-797.
Arora et al., "Perspectives in Pharmacology: Role of Tyrosine Kinase Inhibitors in Cancer Therapy," *Jounral of Pharmacology and Experimental Therapeutics*, 2005; 315:971-979.
Bagrov et al., "N-[Hydroxy(amino)alkyl]amides of Amino(nitro)benzoic Acids", *Russian Journal of Organic Chemistry*, 2000; 36:674-678.
Barr et al. "Polo-Like Kinases and The Orchestration of Cell Division", *Molecular Cell Biology, Nature Reviews*, 2004; 5:429-440.
Bettencourt-Dias, et al. "SAK/PLK4 is Required for Centriole Duplication and Flagella Development", *Current Biology*, 2005; 15:2199-2207.
Bolen et al., "Nonreceptor tyrosine protein kinases" *Oncogene*, 1993; 8:2025-2031.
Boyce et al., "Requirement of pp60$^{c-src}$ Expression for Osteoclasts to Form Ruffled Borders and Resorb Bone in Mice" *J.Clin. Invest.*, 1992; 90:1622-1627.
Bradshaw, "Cell transformation: the role of oncogenes and factors" *Mutagenesis*, 1986; 1:91-97.
Brown et al., "Regulation, substrates and functions of src" *Biochimica et Biophysica Acta*, 1996; 1287:121-149.
Brown et al., "FlashPlate™ Technology-Principles and Characteristics of Flashplate Scintillation Counting", *High Throughput Screening, The Discovery of Bioactive Substances*, 1997; 317-328.
Burke, "Protein-Tyrosine Kinase Inhibitors", *Drugs of the Future*, 1992; 17: 119-131.
Brunton et al., "A role for epidermal growth factor receptor, c-Src and focal adhesion kinase in an in vitro model for the progression of colon cancer" Oncogene, 1997; 14:283-293.
Burns, et al. "Silencing of the Novel p53 Target Gene Snk/Plk2 Leads to Mitotic Catastrophe in Paclitaxel (Taxol)-Exposed Cells", *Molecular and Cellular Biology*, 2003; 23:5556-5571.
Calderwood et al., "Pyrrolo[2,3-d]pyrimidines Containing Diverse N-7 Substituents as Potent Inhibitors of Lck", *Bioorganic & Medicinal Chemistry Letters*, 2002; 12: 1683-1686.
Cardiello et al., "Epidermal Growth Factor Receptor Tyrosine Kinase Inhibitors in Late Stage Clinical Trials", *Oncologic, Endocrine & Metabolic, Expert Opinion*, 2003; 8(2): 501-514.
Carvajal et al., "Aurora Kinases: New Targets for Cancer Therapy", *Clinical Cancer Research*, 2006; 12:6869-6875.
Castedo et al., "Cell death by mitotic catastrophe: a molecular definition." *Oncogene*, 2004; 23: 2825-2837.

(56) References Cited

OTHER PUBLICATIONS

Cartwright et al., "Activation of the pp600-5rc protein kinase in an early event in colonic carcinogenesis" Proc. Natl. Acad. Sci., 1990; 87:558-562.
Coghlan et al., "Selective small molecule inhibitors of glycogen synthase kinase-3 modulate glycogen metabolism and gene transcription", *Chemistry & Biology*, 2000; 7:793-803.
Cohen et al., "The renaissance of GSK3", *Nature Reviews: Molecular Cell Biology*, 2001; 2:769-776.
Collins et al., "The Chemotherapy of Schistosomiasis. Part IV. Some Ethers of 4-Amino-2-methoxyphenol", *Journal of the Chemical Society*, 1961: 1863-1879.
Cook et al., "Scintillation Proximity Enzyme Assay. A Rapid and Novel Assay Technique Applied to HIV Proteinase", *Structure and Function of the Aspartic Proteinases*, 1991: 525-528.
Courtneidge et al., "Protein tyrosine kinases, with emphasis on the Src family" Semin. Cancer Biol., 1994; 5:239-246.
Cross et al., "Selective small-molecule inhibitors of glycogen synthase kinase-3 activity protect primary neurons from death", *Journal of Neurochemistry*, 2001; 77:94-102.
Dai et al., "Tyrosine Kinase Etk/BMX is Up-Regulated in Human Prostate Cancer and Its Overexpression Induces Prostate Intraepithelial Neoplasia in Mouse", *Cancer Research*, 2006; 66: 8058-8064.
Davies et al, "Specificity and Mechanism of Action of Some Commonly Used Protein Kinase Inhibitors", *Biochem J.*, 2000; 351: 95-105.
Delia et al., "Fused Pyrimidines Part Four: Miscellaneous Fused Pyrimidines", *The Chemistry of Heterocyclic Compounds, A Series of Monographs*, 1992: 261-305.
Druker et al., "Lessons Learned From the Development of an Abl Tyrosine Kinase Inhibitor for Chronic Myelogenous Leukemia", *The Journal of Clinical Investigations*, 2000; 105: 3-7.
Dumont et al. "Cardiovascular Failure in Mouse Embryos Deficient in VEGF Receptor-3", *Science*, 1998; 282:946-949.
Elder et al., "Overexpression of Transforming Growth Factor α in Psoriatic Epidermis", *Science*, 1989; 243: 811-814.
Embi et al., "Glycogen Synthase Kinase-3 from Rabbit Skeletal Muscle Separation from Cyclic-AMP-Dependent Protein Kinase and Phosporylase Kinase", *Eur. J. Biochem.*, 1980; 107: 519-527.
Fanning et al., "Elevated Expression of pp60c-src in Low Grade Human Bladder Carcinomas" Cancer Research, 1992; 52:1457-1462.
Furuta et al, "Molecular Design of Glutathione-Derived Biochemical Probes Targeting the GS-X Pump", Tetrahedron, 1999; 55: 7529-7540.
Fode et al. "Sak, a Murine Protein-Serine/Threonine Kinase that is Related to the Drosophila Polo Kinase and Involved in Cell Proliferation", *Proc. Natl. Acad. Sci*, 1994; 9: 6388-6392.
Grimminger et al., "Targeting non-malignant disorders with tyrosine kinase inhibitors", *Nature Review: Drug Discovery*, 2010; 9: 856-870.
Hanks et al., "Signaling through focal adhesion kinase" BioEssays, 1997; 19:137-145.
He et al., "Suppression of Tumor Lymphangiogenesis and Lymph Node Metastasis by Blocking Vascular Endothelial Growth Factor Receptor 3 Signaling", *Journal of the National Cancer Institute*, 2002; 94:819-824.
Hennequin et al., "Novel-4 Anilinoquinazolines with C-7 Basic Side Chains: Design and Structure Activity Relationship of a Series of Potent, Orally Active, VEGF Receptor Tyrosine Kinase Inhibitors", *Journal of Medicinal Chemistry*, 2002; 45:1300-1312.
International Search Report from PCT/EP2004/005621, dated Oct. 27, 2004.
International Search Report from PCT/EP2004/053497, dated Apr. 12, 2005.
International Search Report from PCT/EP2004/053501, dated Apr. 28, 2005.
International Search Report from PCT/EP2005/056606, dated Apr. 3, 2006.
International Search Report from PCT/EP2005/056609, dated May 26, 2005.
International Search Report from PCT/EP2006/063555, dated Feb. 21, 2008.
International Search Report from PCT/EP2007/061499, dated Jul. 30, 2008.
International Search Report from PCT/EP2008/059833, dated Oct. 23, 2008.
International Search Report from PCT/EP2009/052692, dated Jun. 9, 2009.
Jankowski et al., "Oncogenes and onco-suppressor gene in adenocarcinoma of the oesophagus" *Gut*, 1992; 33:1033-1038.
Kaidanovich et al. "The role of glycogen synthase kinase-3 in insulin resistance and Type 2 diabetes", *Expert Opinion on Therapeutic Targets*, 2002; 6:555-561.
Kaipainen et al. "Expression of the fms-Like Tyrosine Kinase 4 Gene Becomes Restricted to Lymphatic Endothelium During Development", *Pro. Natl. Acad. Sci.*, 1995; 92:3566-70.
Karkkainen et al. "Lymphatic Endothelial Regulation, Lymphoedema, and Lymph Node Metastasis", *Cell & Developmental Biology*, 2002; 13:9-18.
Karn et al. "Human SAK Related to the PLK/polo Family of Cell Cycle Kinases Shows High mRNA Expression in testis", *Oncology Reports*, 1997; 5:505-510. (Abstract Only).
Kawato et al., "Novel Pepitdomimetics of the Antifungal Cyclic Peptide Rhodopeptin: Synthesis of Mimetics and Their Antifungal Activity", *Organic Letters*, 2001; 3: 3451-3454.
Klinghoffer et al., "Src family kinases are required for integrin but not PDGFR signal transduction" EMBO Journal, 1999; 18:2459-2471.
Kuo et al., Synthesis and Identification of [1,3,5]Triazine-pyridine Biheteroaryl as a Novel Series of Potent Cyclin-Dependent Kinase Inhibitors, *J. Med. Chem.*, 2005; 48: 4535-4546.
Kypta, "GSK-3 inhibitors and their potential in the treatment of Alzheimer's disease", *Expert Opinion on Therapeutic Patents*, 2005; 15: 1315-1331.
Larson et al., "Chapter 13. New Approaches to Antitumor Therapy", Ann. Reports in Med. Chem., 1989; 24:121-128.
Lauffenburger et al., "Cell Migration: A Physically Integrated Molecular Process", Cell, 1996; 84:359-369.
Li, et al., "SAK, A New Polo-Like Kinase, is Transcriptionally Repressed by p53 and Induces Apoptosis upon RNAi Silencing", *Neoplasia*, 2005; 7: 312-323.
Liotta et al. "Tumor Invasion and Metastases: Biochemical Mechanisms", *Cancer Treatment and Research*, 1988; 40:223-238.
Lutz et al., "Overexpression and Activation of the Tyrosine Kinase Src in Human Pancreatic Carcinoma" Biochem. and Biophys. Res. Comm., 1998; 243:503-508.
Mackay et al., "A phase II trial of the Src kinase inhibitor AZD0530 in patients with metastatic or locally advanced gastric or gastroesophageal junction (GEJ) adenocarcinoma: A trial of the PMH phase II consortium", 2010 ASCO Annual Meeting, *J Clin Onco* 28(suppl): abstract e14544.
Mao et al., "Activation of c-Src by receptor tyrosine kinases in human colon cancer cells with high metastatic potential" *Oncongene*, 1997; 15:3083-3090.
Mazurenko et al., "Expression of pp60$^{c\text{-}src}$ in human small cell and non-small cell lung carcinomas" *European Journal of Cancer*, 1992; 28:372-377.
Morin, "Oncogene to Drug: Development of Small Molecule Tyrosine Kinase Inhibitors as Anti-Tumor and Anti-Angiogenic Agents", *Oncogene*, 2000; 19:6574-6583.
Murphy et al., "Intramolecular Termination of Radical-Polar Crossover Reactions", *Journal of the Chemical Society Perkin Transactions 1*, 1998; 15:2331-2339.
Muthuswamy et al., "Activation of Src family kinases in Neu-induced mammary tumors correlates with their asociation with distinct sets of tyrosine phosphorylated proteins in vivo" Oncogene, 1995; 11:1801-1810.
Nagamatsu et al., "General Syntheses of 1-Alkyltoxoflavin and 8-Alkylfervenulin Derivatives of Biological Significance by the Regioselective Alkylation of Reumycin Derivatives and the Rates of Transalkylation From 1-Alkyltoxoflavins Into Nucleophiles", *J. Chem. Soc., Perkin Trans. 1*, 2001: 130-137.

(56) References Cited

OTHER PUBLICATIONS

Nagamatsu et al., "Syntheses Of 3-Substituted 1-Methyl-6-Phenylprimido[5,4-e]-1,2,4-Triazine-5,7(1 H,6H)-Diones (6-Phenyl Analogs of Toxoflavin) and Their 4-Oxides, and Evaluation of Antimicrobial Activity of Toxoflavins and Their Analogs", *Chem. Pharm. Bull*, 1993; 41:362-368.

Nicolson et al., "Cancer Metastasis: Tumor Cell and Host Organ Properties Important in Metastasis to Specific Secondary Sites", *Biochimica et Biophysica Acta*, 1988; 948: 175-224.

Norman, "Emerging Fundamental Themes in Modern Medicinal Chemistry", *Drug News Perspect*, 2001; 14: 242-247.

Ny et al., "A Genetic Xenopus Laevis Tadpole Model to Study Lymphangiogenesis", *Nature Medicine*, 2005; 11:998-1004.

Owens et al., "The catalytic activity of the Src family kinases is required to disrupt cadherin-dependent cell-cell contacts" *Molecular Biology of the Cell*, 2000; 11:51-64.

Palmer et al., "Tyrosine Kinase Inhitors. II. Soluble Analogues of Pyrrolo- and Pyrazoloquinazolines as Epidermal Growth Factor Receptor Inhibitors: Synthesis, Biological Evaluation, and Modeling of the Mode of Binding", *Journal of Medicinal Chemistry*, 1997; 40: 1519-1529.

Parsons et al., "Src family protein tyrosine kinases: cooperating with growth factor and adhesion signaling pathways" *Current Opinion in Cell Biology*, 1997; 9:187-192.

Pleixats et al., "The Search for New Biochemical Photoprobes. The Nucleophilic Photosubstitution of 2-Fluoro-4-Nitronisole", *Tetrahedron*, 1989; 45: 7817-7826.

Prichard et al., "The prevention of breast cancer," *British Journal of Surgery*, 2003; 90: 772-783.

Rusnak et al., "The characterization of novel, dual ErbB-2/EGFR, tyrosine kinase inhibitors: potential therapy for cancer", *Cancer Research*, 2001; 61: 7196-7203.

Saito et al., "Fyn: A Novel Molecular Target in Prostate Cancer", *Cancer*, 2010; 116: 1629-1637.

Schlaepfer et al., "Signaling through focal adhesion kinase" *Progress in Biophysics and Molecular Biology*, 1999; 71:435-478.

Shawver et al., "Smart Drugs: Tyrosine Kinase Inhibitors In Cancer Therapy", *Cancer Cell*, 2002; 1:117-123.

Skobe et al. "Induction of Tumor Lymphangiogenesis by VEGF-C Promotes Breast Cancer Metastasis", *Nature Medicine*, 2001; 7: 192-198.

Spankuch-Schmitt et al., "Downregulaton of Human Polo-Like Kinase Activity by Antisense Oligonucleotides Induces Growth Inhibitor in Cancer Cells", *Oncogene*, 2002; 21: 3162-3171.

Stacker et al., "The Role of Tumor Lymphangiogenesis in Metastatic Spread", *FASEB J.*, 2002; 9:922-934.

Thiel, "Structure-aided drug design's next generation", 2004; *Nature Biotechnol* 22: 513-519.

Ullrich et al., "Signal transduction by receptors with tyrosine kinase activity" *Cell*, 1990; 61:203-212.

Underiner et al., "Development of Vascular Endothelial Growth Factor Receptor (VEGFT) Kinase Inhibitors as Anti-Angiogenic Agents in Cancer Therapy", *Current Medicinal Chemistry*, 2004; 11: 731-745.

Verbeek et al., "Overexpression of c-Src enhances cell-matrix adhesion and cell migration in PDGF-stimulated NIH3T3 fibroblasts" *Exp. Cell Res.*, 1999; 248(2):531-537.

Von Pawel, "Gefitinib (Iressa, ZD1839): a novel targeted approach for the treatment of solid tumors," *Bull. Cancer*, 2004; 91(5):E70-E76.

Wang et al., "Cell Cycle Arrest and Apoptosis Induced by Human Polo-Like Kinase 3 Is Mediated through Perturbation of Microtubule Integrity", *Molecular and Cellular Biology*, 2002: 22:3450-3459.

Wedge et al. "ZD6474 Inhibits Vascular Endothelial Growth Factor Signaling, Angiogenesis, and Tumor Growth Following Oral Administration", *Cancer Research*, 2002; 62: 4645-55.

Wiener et al., "Decreased Src tyrosine kinase activity inhibits malignant human ovarian cancer tumor growth in a nude mouse model" *Clin. Cancer Res.*, 1999; 5:2164-2170.

Wilks, "Protein tyrosine kinase growth factor receptors and their ligands in development, differentiation, and cancer" *Adv. Cancer Res.*, 1993; 60:43-73.

Wissner et al., "4-Anilino-6,7-dialkoxyquinoline-3-carbonitrile Inhibitors of Epidermal Growth Factor Receptor Kinase And Their Bioisosteric Relationship To The 4-Anilino-6,7-dialkoxyquinazoline Inhibitors", *Journal of Medicinal Chemistry*, 2000, 43: 3244-3256.

Wright et al., "Anilinoquinazoline Inhibitors of Fructose 1,6-Bisphosphate Bind at a Nove Allosteric Site: Synthesis, in vitro Characterizations, and X-ray Crystallography", *J. Med. Chem.*, 2002; 45: 3865-3877.

Yang et al., "Inhibition of Epidermal Growth Factore Receptor Tyrosine Kinase by Chalcone Derivatives," *Biochimica et Biophysica Acta*, 2001; 1550: 144-152.

Yarden et al., "Growth factor receptor tyrosine kinases" *Ann. Rev. Biochem.*, 1988; 57:443-478.

Yoneda et al., "Herbimycin A, a pp60c-src tyrosine kinase inhibitor, inhibits osteoclastic bone resorption in vitro and hypercalcemia in vivo" *J. Clin. Invest.*, 1993; 91:2791-2795.

Yuan et al. "Efficient Internalization of the Polo-Box of Polo-Like Kinase 1 Fused to an Antennapedia Peptide Results in Inhibition of Cancer Cell Proliferation", *Cancer Research*, 2002; 62:4186-4190.

Zeneca Ltd., "4-Anilinoquinazoline Derivatives", *Expert Opinion on Therapeutic Patents*, 1998; 8: 475-478.

Zetter et al., "The Cellular Basis of Site-Specific Tumor Metastasis", *N. Engl. J. Med.*, 1990; 322: 605-12.

\* cited by examiner

PYRIDO-AND PYRIMIDOPYRIMIDINE DERIVATIVES AS ANTI-PROLIFERATIVE AGENTS

CROSS-REFERENCED TO RELATED APPLICATIONS

This application is a Divisional of U.S. patent application Ser. No. 10/596,512 filed on Jun. 15, 2006, now U.S. Pat. No. 7,799,772, which is the national stage of PCT Application No. PCT/EP2004/053501, filed Dec. 15, 2004, which application claims priority from PCT Patent Application No. PCT/EP03/51062, filed Dec. 18, 2003 and PCT Patent Application No. PCT/EP03/51058, filed Dec. 18, 2003. All of the above applications are incorporated herein by reference in their entirety.

This invention relates to pyrimidopyrimidine derived macrocycles that have been found to possess anti-proliferative activity, such as anti-cancer activity and are accordingly useful in methods of treatment of the human or animal body, for example in the manufacture of medicaments for use in hyper proliferative disorders such as atherosclerosis, restenosis and cancer. The invention also relates to processes for the manufacture of said pyrimidopyrimidine derivatives, to pharmaceutical compositions containing them and to their use in the manufacture of medicaments of use in the production of anti-proliferative effect.

In particular, the compounds of the present invention were found to inhibit tyrosine kinase enzymes, also called tyrosine kinases. Tyrosine kinases are a class of enzymes, which catalyse the transfer of the terminal phosphate of adenosine triphosphate to the phenolic hydroxyl group of a tyrosine residue present in the target protein. It is known, that several oncogenes, involved in the transformation of a cell into a malignant tumour cell, encode tyrosine kinase enzymes including certain growth factor receptors such as EGF, FGF, IGF-1R, IR, PDGF and VEGF. This family of receptor tyrosine kinases and in particular the EGF family of receptor tyrosine kinases are frequently present in common human cancers such as breast cancer, non-small cell lung cancers including adenocarcinomas and squamous cell cancer of the lung, bladder cancer, oesophageal cancer, gastrointestinal cancer such as colon, rectal or stomach cancer, cancer of the prostate, leukaemia and ovarian, bronchial or pancreatic cancer, which are examples of cell proliferation related disorders.

Accordingly, it has been recognised that the selective inhibition of tyrosine kinases will be of value in the treatment of cell proliferation related disorders. Support for this view is provided by the development of Herceptin® (Trastuzumab) and Gleevec™ (imatinib mesylate) the first examples of target based cancer drugs. Herceptin® (Trastuzumab) is targeted against Her2/neu, a receptor tyrosine kinase found to be amplified up to 100-fold in about 30% of patients with invasive breast cancer. In clinical trials Herceptin® (Trastuzumab) proved to have anti-tumour activity against breast cancer (Review by L. K. Shawer et al, "Smart Drugs: Tyrosine kinase inhibitors in cancer therapy", 2002, Cancer Cell Vol. 1, 117), and accordingly provided the proof of principle for therapy targeted to receptor tyrosine kinases. The second example, Gleevec™ (imatinib mesylate), is targeted against the abelson tyrosine kinase (BcR-Abl), a constitutively active cytoplasmic tyrosine kinase present in virtually all patients with chronic myelogenous leukaemia (CML) and 15% to 30% of adult patients with acute lymphoblastic leukaemia. In clinical trials Gleevec™ (imatinib mesylate) showed a spectacular efficacy with minimal side effects that led to an approval within 3 months of submission. The speed of passage of this agent through clinical trials and regulatory review has become a case study in rapid drug development (Drucker B. J. & Lydon N., "Lessons learned from the development of an Abl tyrosine kinase inhibitor for chronic myelogenous leukaemia.", 2000, J. Clin. Invest. 105, 3).

Further support is given by the demonstration that EGF receptor tyrosine kinase inhibitors, specifically attenuates the growth in athymic nude mice of transplanted carcinomas such as human mammary carcinoma or human squamous cell carcinoma (Review by T. R. Burke Jr., Drugs of the Future, 1992, 17, 119). As a consequence, there has been considerable interest in the development of drugs to treat different cancers that target the EGFR receptor. For example, several antibodies that bind to the extra-cellular domain of EGFR are undergoing clinical trials, including Erbitux™ (also called C225, Cetuximab), which was developed by Imclone Systems and is in Phase III clinical trials for the treatment of several cancers. Also, several promising orally active drugs that are potent and relatively specific inhibitors of the EGFR tyrosine kinase are now well advanced in clinical trials. The AstraZeneca compound ZD1839, which is now called IRESSA® and approved for the treatment of advanced non-small-cell lung cancer, and the OSI/Genentech/Roche compound OSI-774, which is now called Tarceva™ (erlotinib), have shown marked efficacy against several cancers in human clinical trials (Morin M. J., "From oncogene to drug: development of small molecule tyrosine kinase inhibitors as anti-tumour and anti-angiogenic agents, 2000, Oncogene 19, 6574).

In addition to the above, EGF receptor tyrosine kinases has been shown to be implicated in non-malignant proliferative disorders such as psoriasis (elder et al., Science, 1989, 243; 811). It is therefore expected that inhibitors of EGF type receptor tyrosine kinases will be useful in the treatment of non-malignant diseases of excessive cellular proliferation such as psoriasis, benign prostatic hypertrophy, atherosclerosis and restenosis.

It is disclosed in International Patent Applications WO 96/07657 & WO97/32880 that pyrimidopyrimidines are useful as inhibitors of tyrosine kinase and in particular of the EGF type receptor tyrosine kinases. Unexpectedly it was found that pyrimidopyrimidine derivatives of the present formula (I) that are different in structure show to have tyrosine kinase inhibitory activity.

It is accordingly an object of the present invention to provide further tyrosine kinase inhibitors useful in the manufacture of medicaments in the treatment of cell proliferative related disorders.

This invention concerns compounds of formula (I)

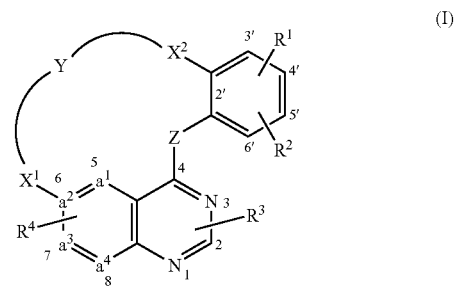

(I)

the N-oxide forms, the pharmaceutically acceptable addition salts and the stereochemically isomeric forms thereof, wherein $a^1$-$a^2$=$a^3$-$a^4$ represents a divalent radical selected from N—CH=CH—CH, N—CH=N—CH or CH—CH=N—CH;

Z represents O, NH or S;

Y represents —$C_{3-9}$alkyl-, —$C_{3-9}$alkenyl-, —$C_{1-5}$alkyl-oxy-$C_{1-5}$alkyl-, —$C_{1-5}$alkyl-NR$^{13}$—$C_{1-5}$alkyl-, —$C_{1-5}$alkyl-NR$^{14}$—CO—$C_{1-5}$alkyl-, —$C_{1-5}$alkyl-CO—NR$^{15}$—$C_{1-5}$alkyl-, —$C_{1-6}$alkyl-CO—NH—, —$C_{1-6}$alkyl-NH—CO—, —CO—NH—$C_{1-6}$alkyl-, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl;

X$^1$ represents a direct bond, O, —O—$C_{1-2}$alkyl-, CO, —CO—$C_{1-2}$alkyl-, NR$^{11}$, —NR$^{11}$—$C_{1-2}$alkyl-, NR$^{16}$—CO—, NR$^{16}$—CO—$C_{1-2}$alkyl-, —O—N=CH— or $C_{1-2}$alkyl;

X$^2$ represents a direct bond, O, —O—$C_{1-2}$alkyl-, CO, —CO—$C_{1-2}$alkyl-, NR$^{12}$, NR$^{12}$—$C_{1-2}$alkyl-, NR$^{17}$—CO—, NR$^{17}$—CO—$C_{1-2}$alkyl-, Het$^{20}$-$C_{1-2}$alkyl-, —O—N=CH— or $C_{1-2}$alkyl;

R$^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo;

R$^2$ represents hydrogen, cyano, halo, hydroxy, hydroxycarbonyl-, Het$^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, Het$^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, Ar$^5$, Ar$^1$-oxy-, dihydroxyborane,
$C_{1-6}$alkoxy- substituted with halo,
$C_{1-4}$alkyl substituted with one or where possible two or more substituents selected from halo, hydroxy or NR$^5$R$^6$,
$C_{1-4}$alkylcarbonyl- wherein said $C_{1-4}$alkyl is optionally substituted with one or where possible two or more substituents selected from hydroxy or $C_{1-4}$alkyl-oxy-;

R$^3$ represents hydrogen, $C_{1-4}$alkyl, cyano or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;

R$^4$ represents hydrogen, hydroxy, Ar$^3$-oxy, Ar$^4$—$C_{1-4}$alkyloxy-, $C_{1-4}$alkyloxy-, $C_{2-4}$alkenyloxy- optionally substituted with Het$^{12}$ or R$^4$ represents $C_{1-4}$alkyloxy substituted with one or where possible two or more substituents selected from $C_{1-4}$alkyloxy-, hydroxy, halo, Het$^2$-, —NR$^7$R$^8$, -carbonyl-NR$^9$R$^{10}$ or Het$^3$-carbonyl-;

R$^5$ and R$^6$ are each independently selected from hydrogen or $C_{1-4}$alkyl;

R$^7$ and R$^8$ are each independently selected from hydrogen, $C_{1-4}$alkyl, Het$^8$, aminosulfonyl-, mono- or di($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, Het$^9$-carbonyl-$C_{1-4}$alkyl-, Het$^{10}$-carbonyl-, polyhydroxy-$C_{1-4}$alkyl-, Het$^{11}$-$C_{1-4}$alkyl- or Ar$^2$—$C_{1-4}$alkyl-;

R$^9$ and R$^{10}$ are each independently selected from hydrogen, $C_{1-4}$alkyl, $C_{3-6}$cycloalkyl, Het$^4$, hydroxy-$C_{1-4}$alkyl-, $C_{1-4}$alkyloxy$C_{1-4}$alkyl- or polyhydroxy-$C_{1-4}$alkyl-;

R$^{11}$ represents hydrogen, $C_{1-4}$alkyl, Het$^5$, Het$^6$-$C_{1-4}$alkyl-, $C_{2-4}$alkenylcarbonyl- optionally substituted with Het$^7$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

R$^{12}$ represents hydrogen, $C_{1-4}$alkyl, $C_{1-4}$alkyl-oxy-carbonyl-, Het$^{17}$, Het$^{18}$-$C_{1-4}$alkyl-, $C_{2-4}$alkenylcarbonyl- optionally substituted with Het$^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

R$^{13}$ represents hydrogen, $C_{1-4}$alkyl, Het$^{13}$, Het$^{14}$-$C_{1-4}$alkyl- or phenyl optionally substituted with one or where possible two or more substituents selected from hydrogen, hydroxy, amino or $C_{1-4}$alkyloxy-;

R$^{14}$ and R$^{15}$ are each independently selected from hydrogen, $C_{1-4}$alkyl, Het$^{15}$-$C_{1-4}$alkyl- or $C_{1-4}$alkyloxy$C_{1-4}$alkyl-;

R$^{16}$ and R$^{17}$ are each independently selected from hydrogen, $C_{1-4}$alkyl, Het$^{21}$-$C_{1-4}$alkyl- or $C_{1-4}$alkyloxy$C_{1-4}$alkyl-;

Het$^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^1$ is optionally substituted with one or where possible two or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

Het$^2$ represents a heterocycle selected from morpholinyl, piperazinyl, piperidinyl, pyrrolidinyl, thiomorpholinyl or dithianyl wherein said Het$^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

Het$^3$, Het$^4$ and Het$^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said Het$^3$, Het$^4$ or Het$^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

Het$^5$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^6$ and Het$^7$ each independently represent a heterocycle selected from morpholinyl, pyrrolidinyl, piperazinyl or piperidinyl wherein said Het$^6$ or Het$^7$ is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^9$ and Het$^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said Het$^9$ or Het$^{10}$ is optionally substituted $C_{1-4}$alkyl, $C_{3-6}$cycloalkyl-$C_{1-4}$alkyl- or amino-$C_{1-4}$alkyl-;

Het$^{11}$ represents a heterocycle selected from indolyl or

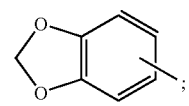

Het$^{12}$ represents a heterocycle selected from morpholinyl, piperazinyl, piperidinyl, pyrrolidinyl, thiomorpholinyl or dithianyl wherein said Het$^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

Het$^{13}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{14}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{15}$ and Het$^{21}$ each independently represent a heterocycle selected from morpholinyl, pyrrolidinyl, piperazinyl or piperidinyl wherein said Het$^{15}$ or Het$^{21}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl;

Het$^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{18}$ and Het$^{19}$ each independently represent a heterocycle selected from morpholinyl, pyrrolidinyl, piperazinyl or piperidinyl wherein said Het$^{18}$ and Het$^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{20}$ represents a heterocycle selected from pyrrolidinyl, 2-pyrrolidinyl, piperidinyl, piperazinyl or pyrazolidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; and Ar$^1$, Ar$^2$, Ar$^3$, Ar$^4$ and Ar$^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

As used in the foregoing definitions and hereinafter,
halo is generic to fluoro, chloro, bromo and iodo;
$C_{1-2}$alkyl defines methyl or ethyl;
$C_{1-3}$alkyl defines straight and branched chain saturated hydrocarbon radicals having from 1 to 3 carbon atoms such as, for example, methyl, ethyl, propyl and the like;
$C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl, 2,2-dimethylethyl and the like;
$C_{1-5}$alkyl defines straight and branched chain saturated hydrocarbon radicals having from 1 to 5 carbon atoms such as, for example, methyl, ethyl, propyl, butyl, pentyl, 1-methylbutyl, 2,2-dimethylpropyl, 2,2-dimethylethyl and the like;
$C_{1-6}$alkyl is meant to include $C_{1-5}$alkyl and the higher homologues thereof having 6 carbon atoms such as, for example hexyl, 1,2-dimethylbutyl, 2-methylpentyl and the like;
$C_{1-7}$alkyl is meant to include $C_{1-6}$alkyl and the higher homologues thereof having 7 carbon atoms such as, for example 1,2,3-dimethylbutyl, 1,2-methylpentyl and the like;
$C_{3-9}$alkyl defines straight and branched chain saturated hydrocarbon radicals having from 3 to 9 carbon atoms such as propyl, butyl, pentyl, hexyl, heptyl, octyl, nonyl and the like;
$C_{2-4}$alkenyl defines straight and branched chain hydrocarbon radicals containing one double bond and having from 2 to 4 carbon atoms such as, for example vinyl, 2-propenyl, 3-butenyl, 2-butenyl and the like;
$C_{3-9}$alkenyl defines straight and branched chain hydrocarbon radicals containing one double bond and having from 3 to 9 carbon atoms such as, for example 2-propenyl, 3-butenyl, 2-butenyl, 2-pentenyl, 3-pentenyl, 3-methyl-2-butenyl, 3-hexenyl and the like;
$C_{2-6}$alkynyl defines straight and branched chain hydrocarbon radicals containing one triple bond and having from 2 to 6 carbon atoms such as, for example, 2-propynyl, 3-butynyl, 2-butynyl, 2-pentynyl, 3-pentynyl, 3-methyl-2-butynyl, 3-hexynyl and the like;
$C_{3-6}$cycloalkyl is generic to cyclopropyl, cyclobutyl, cyclopentyl and cyclohexyl;
$C_{1-4}$alkyloxy defines straight or branched saturated hydrocarbon radicals such as methoxy, ethoxy, propyloxy, butyloxy, 1-methylethyloxy, 2-methylpropyloxy and the like;
$C_{1-6}$alkyloxy is meant to include $C_{1-4}$alkyloxy and the higher homologues such as methoxy, ethoxy, propyloxy, butyloxy, 1-methylethyloxy, 2-methylpropyloxy and the like;
polyhydroxy-$C_{1-4}$alkyl is generic to a $C_{1-4}$alkyl as defined hereinbefore, having two, three or were possible more hydroxy substituents, such as for example trifluoromethyl.

As used in the foregoing definitions and hereinafter, the term formyl refers to a radical of formula —CH(=O). When X$^1$ or X$^2$ represents the divalent radical —O—N=CH—, said radical is attached with the carbon atom to the R$^3$, R$^4$ bearing cyclic moiety, respectively the R$^1$, R$^2$ bearing phenyl moiety of the compounds of formula (I).

The heterocycles as mentioned in the above definitions and hereinafter, are meant to include all possible isomeric forms thereof, for instance pyrrolyl also includes 2H-pyrrolyl; triazolyl includes 1,2,4-triazolyl and 1,3,4-triazolyl; oxadiazolyl includes 1,2,3-oxadiazolyl, 1,2,4-oxadiazolyl, 1,2,5-oxadiazolyl and 1,3,4-oxadiazolyl; thiadiazolyl includes 1,2,3-thiadiazolyl, 1,2,4-thiadiazolyl, 1,2,5-thiadiazolyl and 1,3,4-thiadiazolyl; pyranyl includes 2H-pyranyl and 4H-pyranyl.

Further, the heterocycles as mentioned in the above definitions and hereinafter may be attached to the remainder of the molecule of formula (I) through any ring carbon or heteroatom as appropriate. Thus, for example, when the heterocycle is imidazolyl, it may be a 1-imidazolyl, 2-imidazolyl, 3-imidazolyl, 4-imidazolyl and 5-imidazolyl; when it is thiazolyl, it may be 2-thiazolyl, 4-thiazolyl and 5-thiazolyl; when it is triazolyl, it may be 1,2,4-triazol-1-yl, 1,2,4-triazol-3-yl, 1,2,4-triazol-5-yl, 1,3,4-triazol-1-yl and 1,3,4-triazol-2-yl; when it is benzothiazolyl, it may be 2-benzothiazolyl, 4-benzothiazolyl, 5-benzothiazolyl, 6-benzothiazolyl and 7-benzothiazolyl.

The pharmaceutically acceptable addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butane-dioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

The pharmaceutically acceptable addition salts as mentioned hereinabove are meant to comprise the therapeutically active non-toxic base addition salt forms which the compounds of formula (I) are able to form. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

Conversely said salt forms can be converted by treatment with an appropriate base or acid into the free acid or base form.

The term addition salt as used hereinabove also comprises the solvates which the compounds of formula (I) as well as the salts thereof, are able to form. Such solvates are for example hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention.

The N-oxide forms of the compounds of formula (I) are meant to comprise those compounds of formula (I) wherein one or several nitrogen atoms are oxidized to the so-called N-oxide.

A preferred group of compounds consists of those compounds of formula (I) wherein one or more of the following restrictions apply:
Z represents NH;
Y represents —$C_{3-9}$alkyl-, —$C_{2-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-6}$alkyl-NH—CO—, —CO—$C_{1-7}$alkyl-, —$C_{1-7}$alkyl-CO— or $C_{1-6}$alkyl-CO—$C_{1-6}$alkyl;
$X^1$ represents O, —O—$C_{1-2}$alkyl-, —O—N=CH—, $NR^{11}$ or —$NR^{11}$—$C_{1-2}$alkyl-; in a particular embodiment $X^1$ represents —$NR^{11}$—, —O— or —O—$CH_2$—;
$X^2$ represents a direct bond, O, —O—$C_{1-2}$alkyl-, —O—N=CH—, $C_{1-2}$alkyl, $NR^{12}$ or $NR^{12}$—$C_{1-2}$alkyl-; in a particular embodiment $X^2$ represents a direct bond, —O—N=CH—, $C_{1-2}$alkyl-, —O—$C_{1-2}$alkyl, —O— or —O—$CH_2$—;
$R^1$ represents hydrogen, cyano, halo or hydroxy, preferably halo;
$R^2$ represents hydrogen, cyano, halo, hydroxy, hydroxycarbonyl-, $C_{1-4}$alkyloxycarbonyl-, $Het^{16}$-carbonyl-, $C_{1-4}$alkyl-, $C_{2-6}$alkynyl-, $Ar^5$ or $Het^1$;

In a further embodiment $R^2$ represents hydrogen, cyano, halo, hydroxy, or $Ar^5$;
$R^3$ represents hydrogen;
$R^4$ represents hydrogen, hydroxy, $C_{1-4}$alkyloxy-, $Ar^4$—$C_{1-4}$alkyloxy or $R^4$ represents $C_{1-4}$alkyloxy substituted with one or where possible two or more substituents selected from
  $C_{1-4}$alkyloxy- or $Het^2$-;
$R^{11}$ represents hydrogen, $C_{1-4}$alkyl- or $C_{1-4}$alkyl-oxy-carbonyl-;
$R^{12}$ represents hydrogen, $C_{1-4}$alkyl- or $C_{1-4}$alkyl-oxy-carbonyl-;
$R^{13}$ represents $Het^{14}$-$C_{1-4}$alkyl, in particular morpholinyl-$C_{1-4}$alkyl;
$Het^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;
$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;
  In a further embodiment $Het^2$ represents a heterocycle selected from morpholinyl or piperidinyl optionally substituted with $C_{1-4}$alkyl-, preferably methyl;
$Het^{14}$ represents a heterocycle selected from morpholinyl, piperazinyl, piperidinyl or pyrrolidinyl wherein said $Het^{14}$ is optionally substituted with one or where possible two or more substituents selected from hydroxy, amino or $C_{1-4}$alkyl-;
$Het^{16}$ represents a heterocycle selected from piperidinyl, morpholinyl or pyrrolidinyl;
$Ar^4$ represents phenyl optionally substituted with cyano, hydroxy-, $C_{1-4}$alkyloxy or $C_{1-4}$alkyl;
$Ar^5$ represents phenyl optionally substituted with cyano, hydroxy, $C_{1-4}$alkyloxy or $C_{1-4}$alkyl.

A further group of compounds consists of those compounds of formula (I) wherein one or more of the following restrictions apply:
Z represents NH;
Y represents —$C_{3-9}$alkyl-, —$C_{1-5}$alkyl-$NR^{13}$—$C_{1-5}$alkyl-, —$C_{1-6}$alkyl-NH—CO— or —CO—NH—$C_{1-6}$alkyl-;
$X^1$ represents —O— or —$NR^{11}$—;
$X^2$ represents a direct bond, —$C_{1-2}$alkyl-, —O—$C_{1-2}$alkyl, —O— or —O—$CH_2$—;
$R^1$ represents hydrogen or halo;
$R^2$ represents hydrogen, cyano, halo, hydroxycarbonyl-, $C_{1-4}$alkyloxycarbonyl-, $Het^{16}$-carbonyl- or $Ar^5$;
$R^3$ represents hydrogen;
$R^4$ represents hydrogen, hydroxy, $C_{1-4}$alkyloxy-, $Ar^4$—$C_{1-4}$alkyloxy or $R^4$ represents $C_{1-4}$alkyloxy substituted with one or where possible two or more substituents selected from
  $C_{1-4}$alkyloxy- or $Het^2$-;
$R^{11}$ represents hydrogen;
$R^{12}$ represents hydrogen, $C_{1-4}$alkyl- or $C_{1-4}$alkyl-oxy-carbonyl-;
$R^{13}$ represents $Het^{14}$-$C_{1-4}$alkyl, in particular morpholinyl-$C_{1-4}$alkyl;
$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;
  In a further embodiment $Het^2$ represents a heterocycle selected from morpholinyl or piperidinyl optionally substituted with $C_{1-4}$alkyl-, preferably methyl;

Het$^{14}$ represents morpholinyl;
Het$^{16}$ represents a heterocycle selected from morpholinyl or pyrrolidinyl;
Ar$^4$ represents phenyl;
Ar$^5$ represents phenyl optionally substituted with cyano.

Another group of compounds consists of those compounds of formula (I) wherein one or more of the following restrictions apply:

Z represents NH;
Y represents —C$_{3-9}$alkyl-, —C$_{2-9}$alkenyl-, —C$_{1-5}$alkyl-oxy-C$_{1-5}$alkyl-, —C$_{1-5}$alkyl-NR$^{13}$—C$_{1-5}$alkyl-, —C$_{1-5}$alkyl-NR$^{14}$—CO—C$_{1-5}$alkyl-, —C$_{1-6}$alkyl-NH—CO—, —CO—C$_{1-7}$alkyl-, —C$_{1-7}$alkyl-CO— or C$_{1-6}$alkyl-CO—C$_{1-6}$alkyl;
X$^1$ represents O, —O—C$_{1-2}$alkyl-, —O—N=CH—, NR$^{11}$ or —NR$^{11}$—C$_{1-2}$alkyl-; in a particular embodiment X$^1$ represents a direct bond, C$_{1-2}$alkyl-, —O—C$_{1-2}$alkyl, —NR$^{11}$—, —O— or —O—CH$_2$—;
X$^2$ represents a direct bond, O, —O—C$_{1-2}$alkyl-, —O—N=CH—, NR$^{17}$—CO—, NR$^{17}$—CO—C$_{1-2}$alkyl-, C$_{1-2}$alkyl, Het$^{20}$—C$_{1-2}$alkyl-, NR$^{12}$ or NR$^{12}$—C$_{1-2}$alkyl-; in a particular embodiment X$^2$ represents a direct bond, C$_{1-2}$alkyl-, —O—C$_{1-2}$alkyl, NR$^{17}$—CO—, NR$^{17}$—CO—C$_{1-2}$alkyl-, Het$^{20}$-C$_{1-2}$alkyl-, —O— or —O—CH$_2$—;
R$^1$ represents hydrogen, cyano, halo or hydroxy, preferably halo;
R$^2$ represents hydrogen, cyano, halo, hydroxy, hydroxycarbonyl-, C$_{1-4}$alkyloxycarbonyl-, Het$^{16}$-carbonyl-, C$_{1-4}$alkyl-, C$_{2-6}$alkynyl-, Ar$^5$ or Het$^1$;
in a further embodiment R$^2$ represents hydrogen, cyano, halo, hydroxy, or Ar$^5$; in a more particular embodiment R$^2$ represents hydrogen or halo;
R$^3$ represents hydrogen;
R$^4$ represents hydrogen, hydroxy, C$_{1-4}$alkyloxy-, Ar$^4$—C$_{1-4}$alkyloxy or R$^4$ represents C$_{1-4}$alkyloxy substituted with one or where possible two or more substituents selected from C$_{1-4}$alkyloxy- or Het$^2$-;
R$^{11}$ represents hydrogen, C$_{1-4}$alkyl- or C$_{1-4}$alkyl-oxy-carbonyl-;
R$^{12}$ represents hydrogen, C$_{1-4}$alkyl- or C$_{1-4}$alkyl-oxy-carbonyl-;
R$^{13}$ represents hydrogen or Het$^{14}$-C$_{1-4}$alkyl, in particular morpholinyl-C$_{1-4}$alkyl;
R$^{14}$ represents hydrogen or C$_{1-4}$alkyl;
R$^{17}$ represents hydrogen, C$_{1-4}$alkyl-, Het$^{21}$-C$_{1-4}$alkyl or C$_{1-4}$alkyl-oxy-C$_{1-4}$alkyl; in particular R$^{17}$ represents hydrogen or C$_{1-4}$alkyl;
Het$^1$ represents thiazolyl optionally substituted with amino, C$_{1-4}$alkyl, hydroxy-C$_{1-4}$alkyl-, phenyl, phenyl-C$_{1-4}$alkyl-, C$_{1-4}$alkyl-oxy-C$_{1-4}$alkyl-, mono- or di(C$_{1-4}$alkyl)amino- or amino-carbonyl-;
Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or C$_{1-4}$alkyl-;
In a further embodiment Het$^2$ represents a heterocycle selected from morpholinyl or piperidinyl optionally substituted with C$_{1-4}$alkyl-, preferably methyl;
Het$^{14}$ represents a heterocycle selected from morpholinyl, piperazinyl, piperidinyl or pyrrolidinyl wherein said Het$^{14}$ is optionally substituted with one or where possible two or more substituents selected from hydroxy, amino or C$_{1-4}$alkyl-;
Het$^{16}$ represents a heterocycle selected from piperidinyl, morpholinyl or pyrrolidinyl;
Het$^{20}$ represents a heterocycle selected from pyrrolidinyl, 2-pyrrolidinyl or piperidinyl;
Het$^{21}$ represents a heterocycle selected from morpholinyl, piperazinyl, piperidinyl or pyrrolidinyl wherein said Het$^2$ is optionally substituted with one or where possible two or more substituents selected from hydroxy, amino or C$_{1-4}$alkyl-;
Ar$^4$ represents phenyl optionally substituted with cyano, hydroxy-, C$_{1-4}$alkyloxy or C$_{1-4}$alkyl;
Ar$^5$ represents phenyl optionally substituted with cyano, hydroxy, C$_{1-4}$alkyloxy or C$_{1-4}$alkyl.

A further group of compounds consists of those compounds of formula (I) wherein one or more of the following restrictions apply:

Z represents NH;
Y represents —C$_{3-9}$alkyl-, —C$_{1-5}$alkyl-NR$^{13}$—C$_{1-5}$alkyl-, —C$_{1-5}$alkyl-NR$^{14}$—CO—C$_{1-5}$alkyl-, —C$_{1-6}$alkyl-NH—CO— or —CO—NH—C$_{1-6}$alkyl-;
X$^1$ represents a direct bond, —C$_{1-2}$alkyl-, —O—C$_{1-2}$alkyl, —O—, —O—CH$_2$— or —NR$^{11}$—;
X$^2$ represents —O—, —O—C$_{1-2}$alkyl, —NR$^{12}$—, NR$^{12}$—C$_{1-2}$alkyl, —NR$^{17}$—CO—, NR$^{17}$—CO—C$_{1-2}$alkyl or Het$^{20}$-C$_{1-2}$alkyl-;
R$^1$ represents hydrogen or halo;
R$^2$ represents hydrogen, cyano, halo, hydroxycarbonyl-, C$_{1-4}$alkyloxycarbonyl-, Het$^{16}$-carbonyl- or Ar$^5$; in particular R$^2$ represents hydrogen or halo;
R$^3$ represents hydrogen;
R$^4$ represents hydrogen, hydroxy, C$_{1-4}$alkyloxy-, Ar$^4$—C$_{1-4}$alkyloxy or R$^4$ represents C$_{1-4}$alkyloxy substituted with one or where possible two or more substituents selected from C$_{1-4}$alkyloxy- or Het$^2$-;
R$^{11}$ represents hydrogen;
R$^{12}$ represents hydrogen, C$_{1-4}$alkyl- or C$_{1-4}$alkyl-oxy-carbonyl-;
R$^{13}$ represents hydrogen or Het$^{14}$-C$_{1-4}$alkyl, in particular hydrogen or morpholinyl-C$_{1-4}$alkyl;
R$^{14}$ represents hydrogen;
R$^{17}$ represents hydrogen;
Het$^2$ represents a heterocycle selected from morpholinyl, piperazinyl, piperidinyl or pyrrolidinyl wherein said Het$^2$ is optionally substituted with one or where possible two or more substituents selected from hydroxy, amino or C$_{1-4}$alkyl-;
In a further embodiment Het$^2$ represents a heterocycle selected from morpholinyl or piperidinyl optionally substituted with C$_{1-4}$alkyl-, preferably methyl;
Het$^{14}$ represents morpholinyl;
Het$^{16}$ represents a heterocycle selected from morpholinyl or pyrrolidinyl;
Het$^{20}$ represents pyrrolidinyl or piperidinyl;
Ar$^4$ represents phenyl;
Ar$^5$ represents phenyl optionally substituted with cyano.
Other special group of compounds are:
those compounds of formula (I0 wherein a$^1$-a$^2$=a$^3$-a$^4$ represents N—CH=CH—CH;
those compounds of formula (I) wherein a$^1$-a$^2$=a$^3$-a$^4$ represents N—CH=N—CH;
those compounds of formula (I) wherein a$^1$-a$^2$=a$^3$-a$^4$ represents CH—CH=N—CH;
those compounds of formula (I) wherein —X$^1$— represents —O—;
those compounds of formula (I) wherein —X$^1$— represents —NR$^{11}$—, in particular —NH—;

those compounds of formula (I) wherein —$X^2$— represents —$NR^{17}$—CO—$C_{1-2}$alkyl-, in particular —NH—CO—$C_{1-2}$alkyl-;

those compounds of formula (I) wherein —$X^2$— represents —$NR^{12}$—$C_{1-2}$alkyl, in particular —NH—$C_{1-2}$alkyl-;

those compounds of formula (I) wherein —Y— represents —$C_{1-5}$alkyl-$NR^{14}$—CO—$C_{1-5}$alkyl-, in particular —$C_{1-5}$alkyl-NH—CO—$C_{1-5}$alkyl-;

those compounds of formula (I) wherein $R^1$ is fluoro, chloro or bromo;

those compounds of formula (I) wherein $R^2$ is fluoro, chloro or bromo;

those compounds of formula (I) wherein $R^1$ and $R^2$ represent halo, in particular those compounds of formula (I) wherein $R^1$ represents fluoro and $R^2$ represents chloro;

those compounds of formula (I) wherein $R^2$ is $Het^1$, in particular thiazolyl optionally substituted with methyl;

those compounds of formula (I) wherein $R^2$ is $C_{2-6}$alkynyl-, in particular ethylene;

those compounds of formula (I) wherein $R^2$ is $Ar^5$, in particular phenyl optionally substituted with cyano;

those compounds of formula (I) wherein $R^3$ is cyano;

those compounds of formula (I) wherein $R^4$ represents methoxy and wherein said methoxy is at position 7 of the structure of formula (I).

those compounds of formula (I) wherein $R^4$ represents $C_{1-4}$alkyloxy substituted with one substituent selected from $C_{1-4}$alkyloxy- or $Het^2$-, in particular propyloxy substituted with morpholinyl;

those compounds of formula (I) wherein $R^{12}$ is hydrogen or $C_{1-4}$alkyl-, in particular methyl or wherein $R^{12}$ is $C_{1-4}$alkyl-oxy-carbonyl-, in particular t-butyl-oxy-carbonyl-;

those compounds of formula (I) wherein $Het^2$ represent morpholinyl optionally substituted with $C_{1-4}$alkyl, preferably morpholinyl attached through the nitrogen atom to the remainder of the compounds of formula (I);

those compounds of formula (I) with $Het^3$ represent morpholinyl optionally substituted with $C_{1-4}$alkyl, preferably morpholinyl attached through the nitrogen atom to the remainder of the compounds of formula (I);

those compounds of formula (I) wherein $Het^{12}$ represent morpholinyl optionally substituted with $C_{1-4}$alkyl, preferably morpholinyl attached through the nitrogen atom to the remainder of the compounds of formula (I).

In a further embodiment of the present invention the $R^1$ substituent is at position 4', the $R^2$ substituent is at position 5', the $R^3$ substituent is at position 2 and the $R^4$ substituent at position 6 of the structure of formula (I). A particular group of compounds according to the present invention are those compounds of formula (I) wherein the aniline fragment is substituted with an $R^2$ substituent at position 5' and an $R^1$ substituent at position 4' and wherein said $R^1$ substituent represents halo, in particular fluoro and wherein said $R^2$ substituent is being selected from the group consisting of halo, $C_{1-4}$alkyloxycarbonyl-, $Het^{16}$-carbonyl-, hydroxycarbonyl-, cyano, or $Ar^5$; in particular said $R^2$ being selected from chloro, bromo, methoxycarbonyl, pyrrolidinocarbonyl, morpholino-carbonyl, hydroxycarbonyl, cyano or phenyl.

The compounds of this invention can be prepared by any of several standard synthetic processes commonly used by those skilled in the art of organic chemistry and described for instance in the following references; "Heterocyclic Compounds"—Vol. 24 (part 4) p 261-304 Fused pyrimidines, Wiley—Interscience; Chem. Pharm. Bull., Vol 41(2) 362-368 (1993); J. Chem. Soc., Perkin Trans. 1, 2001, 130-137.

In brief, for those compounds of formula (I) where —$X^1$— represents —NH— said compounds are generally prepared by reacting the 4-chloro-6-fluoro-pyridopyrimidines or 4,6-dichloro-pyridopyrimidines of formula (II) with an appropriate aniline (III) using art known reaction conditions, such as for example using a base such as triethylamine, N-ethyl-N-(1-methylethyl)-2-propaneamine (DIPEA) and alike or an inorganic base such as $Na_2CO_3$, $K_2CO_3$ and alike in a suitable polar solvent such as propane-2-ol, 1-butanol, acetonitrile and alike at elevated temperatures (60-90° C. or reflux temperatures). The thus obtained anilinopyridopyrimidens (IV) are in a further step substituted by a suitable amine of formula (VII) to give the intermediate of formula VIII. This second substitution reaction is performed under known reactions conditions, such as for example, by stirring the reagentia at an elevated temperature (70-100° C.) optionally in an appropriate solvent such as propane-2-ol, 1-butanol or DMSO in the presence of a base such as for example triethylamine, N-ethyl-N-(1-methylethyl)-2-propaneamine (DIPEA) and alike. The compounds according to the invention are finally obtained after deprotection and ring closure using art known conditions. Ring closure is typically performed in the presence of a coupling reagent such as for example 1,3-dicyclohexylcarbodiimide (DCC), N,N'-carbonyldiimidazole (CDI), $POCl_3$, $TiCl_4$, sulfur chloride fluoride ($SO_2ClF$) or 1-(3-dimethylaminopropyl)-3-ethylcarbodiimide (EDCI) in the presence or absence of hydroxybenzotrialzole (HOBt).

Scheme 0

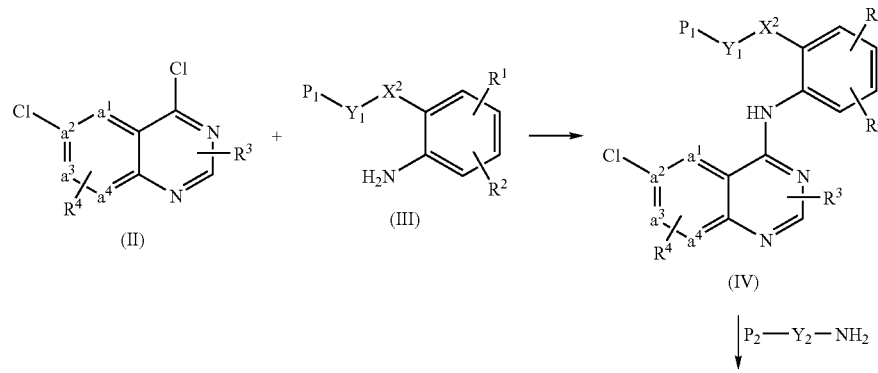

-continued

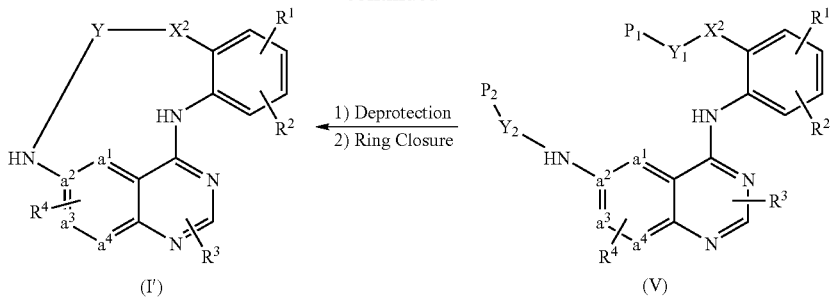

P₁ and P₂ each independently represent optionally protected functional groups, such as for example a primary or secondary amine, hydroxyl, hydroxycarbonyl, or halo (Cl, Br or I), which upon reaction produce together with the $Y_1$ respectively $Y_2$ substituents to which they are attached, the divalent Y radical as defined for the compounds of formula (I)

with an appropriate alkoxide, such as for example benzyloxide, methoxide, 2-trimethylsilylethanol, should give upon deprotection, respectively catalytic hydrogenation, TMSCl, Na₂S, TFA, the desired Mitsunobu precursor of formula (VI) (Scheme 1). Next, ring closure under Mitsunobu conditions give the target compounds (I').

Scheme 1

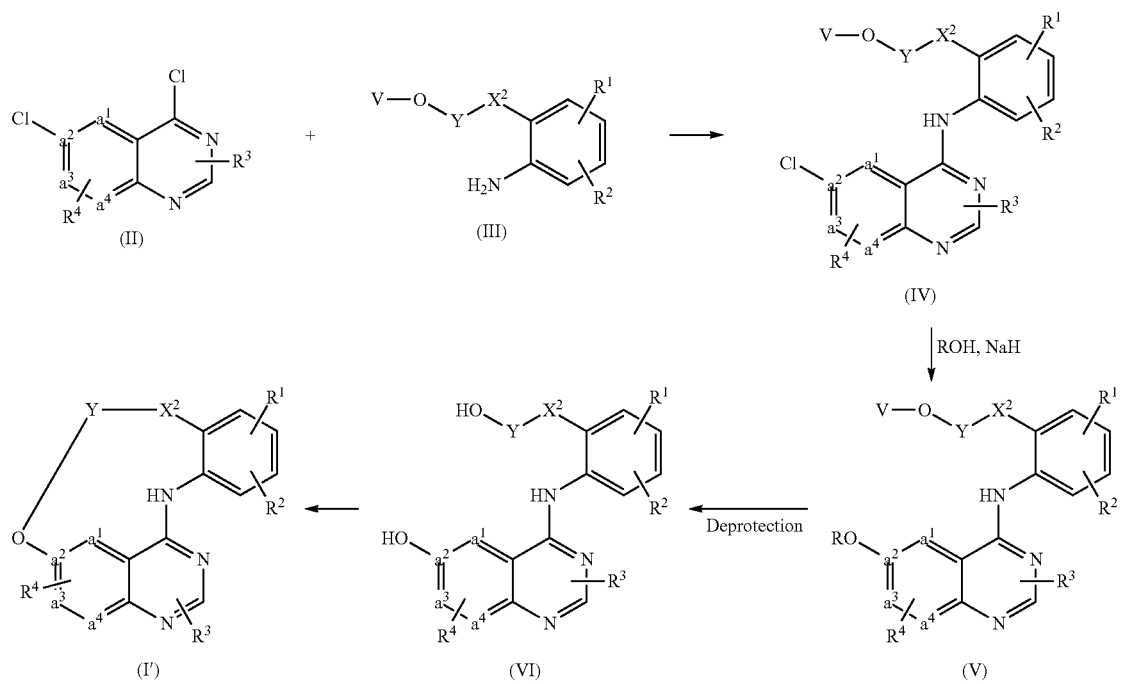

V = hydrogen or a protective group such as for example, methylcarbonyl, t-butyl, methyl, ethyl, benzyl or trialkylsilyl groups; R represents benzyl or methyl; and $a^1-a^2 = a^3-a^4$, Y, $X^2$, $R^1$, $R^2$, $R^3$ and $R^4$ are defined as for the compounds of formula (I)

hereinbefore. $X^1$, $X^2$, $R^1$, $R^2$, $R^3$ and $R^4$ are defined as for the compounds of formula (I) hereinbefore.

As further exemplified in the experimental part of the description, the group of compounds of formula (I) were —$X^1$— represents —O—, hereinafter referred to as compounds of formula (I'), are generally prepared using the following synthesis scheme. The compounds of this invention may be prepared by coupling the known 4-chloro-6-chloro-pyrimidopyrimidine (II) with suitable substituted anilines (III), which in their turn can be prepared according to reaction schemes 3-7, furnish the intermediate compounds (IV). Substitution under art known conditions of the 6-chloro group Those compounds of formula (I'), where $X^2$ represents —O— and $a^1-a^2=a^3-a^4$ represents N—C=N—C are prepared by coupling the known 8-chloro-2(methylthio)-pyrimido[5,4-d]pyrimidine (XXVII) with 2-aminophenol derivatives of formula (XXVIII) yielding the intermediate compounds of formula (XXIX). Next, after protection of the phenol and oxidation of the methylthio, the pyrimidopyrimidine of formula (VIII) is converted into the intermediate of formula (IX) using the appropriate alkoxide. Subsequent deprotection followed by ring closure under Mitsunobu conditions should give the target compounds of formula (I").

Scheme 2

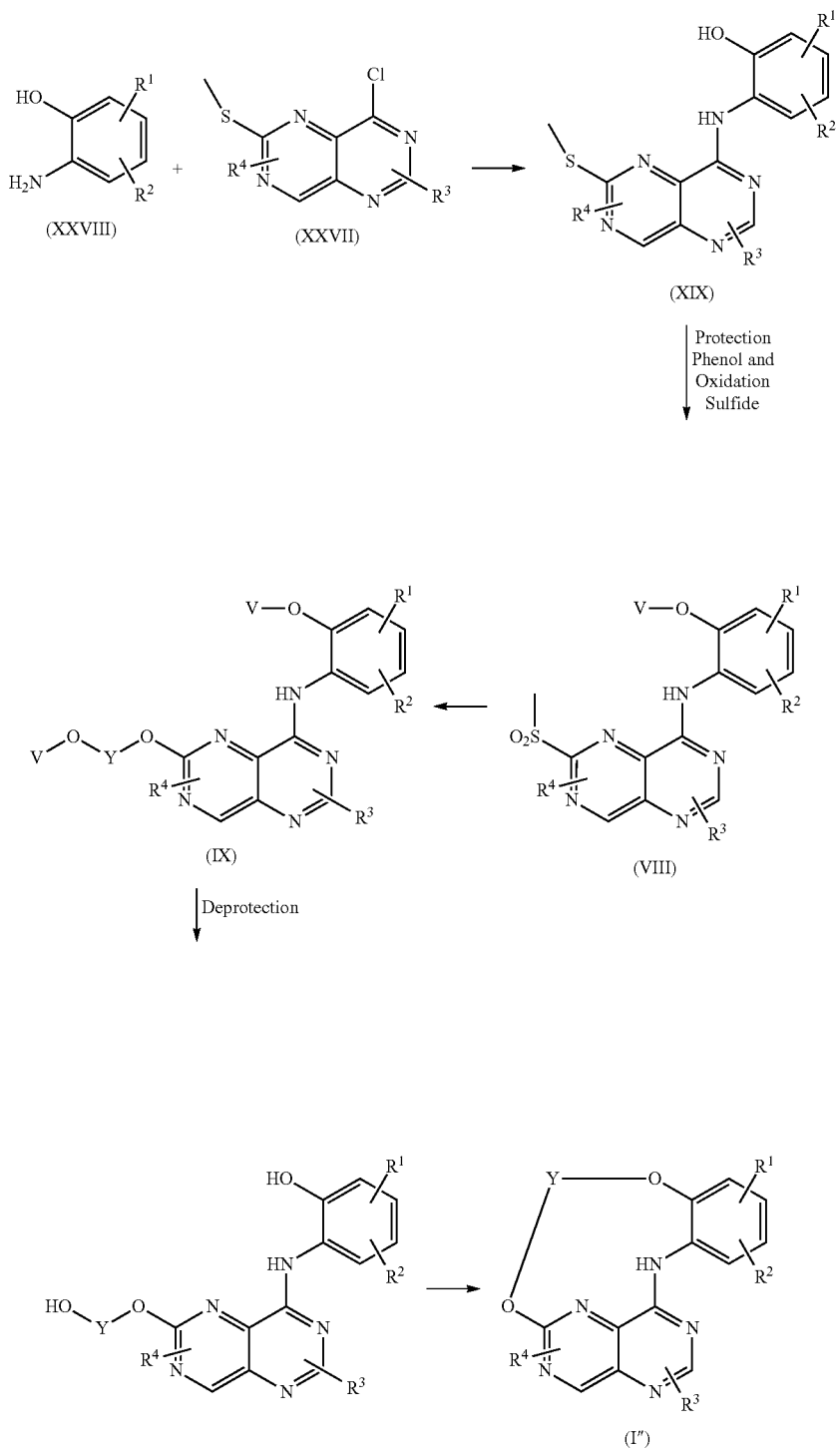

V = hydrogen or a protective group such as for example, methylcarbonyl, t-butyl, methyl, ethyl, benzyl or trialkylsilyl groups; and Y, $X^2$, $R^1$, $R^2$, $R^3$ and $R^4$ are defined as for the compounds of formula (I)

Alternatively, those compounds of formula (I'), where $X^2$ represents —O— and $a^1$-$a^2$=$a^3$-$a^4$ represents C—C=C—N, said compounds are prepared by coupling the known 4-chloro-6-fluoropyridopyrimidines (II) with 2-aminophenol derivatives of formula (XXVIII) yielding the intermediate compounds of formula (VII). Next, after protection of the phenol, the pyridopyrimidine of formula (VIII) is converted into the intermediate of formula (IX) using the appropriate alkoxide. Subsequent deprotection followed by ring closure under Mitsunobu conditions should give the target compounds of formula (I'').

Scheme 3

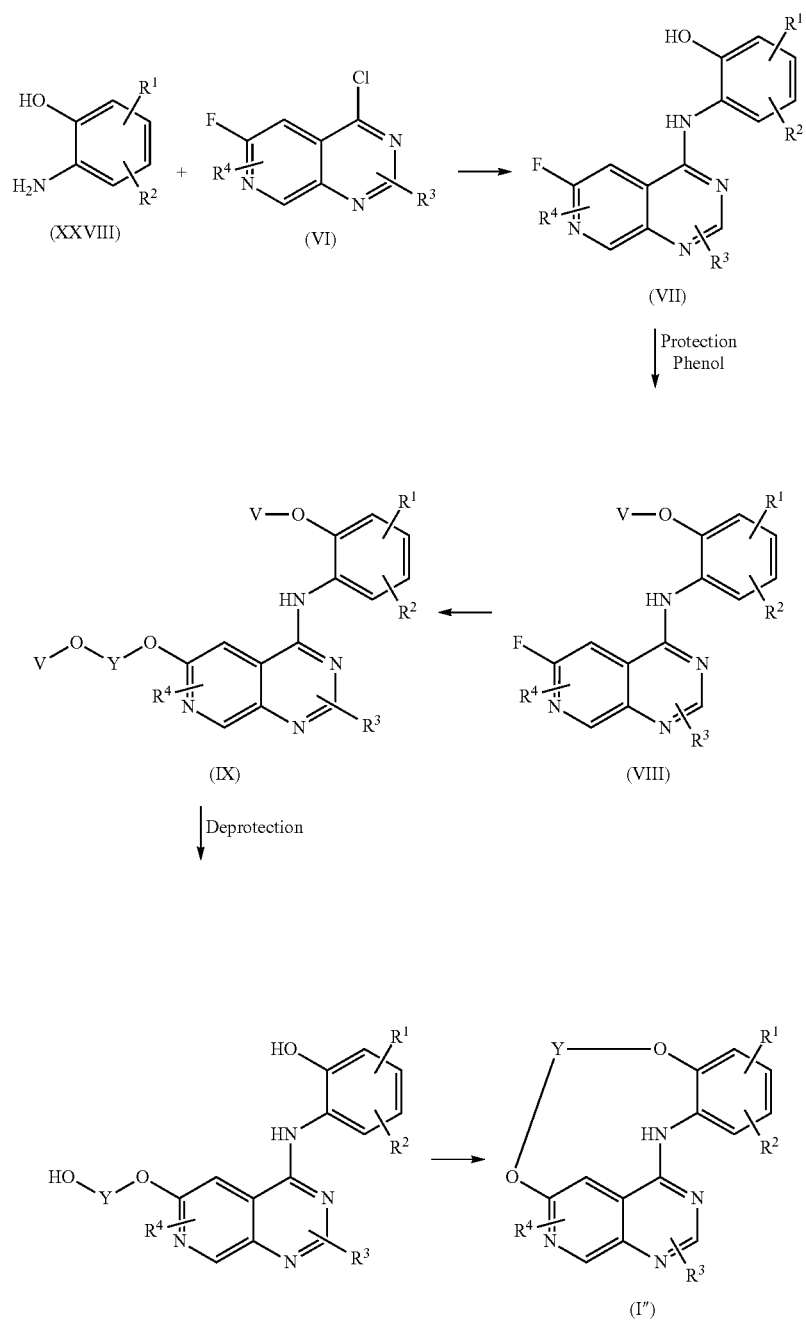

V = hydrogen or a protective group such as for example, methylcarbonyl, t-butyl, methyl, ethyl, benzyl or trialkylsilyl groups; and Y, $R^1$, $R^2$, $R^3$ and $R^4$ are defined as for the compounds of formula (I)

For those compounds where $X^2$ represents —O—, the suitable substituted anilines of formula (III$^a$) are generally prepared from the commercially available nitro-phenols (X) and the α, ω-protected halogenated alcohols (XI) under alkaline conditions in a reaction inert solvent, for example, using dimethylacetamide (DMA) in the presence of $K_2CO_3$. The resulting nitro-phenyl derivative (XII) is subsequently reduced according to standard conditions, for example, using iron/acetic acid, to yield the substituted anilines of formula (III$^a$) (Scheme 4).

Scheme 4

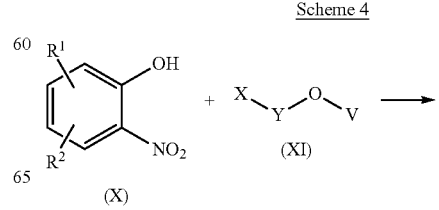

-continued

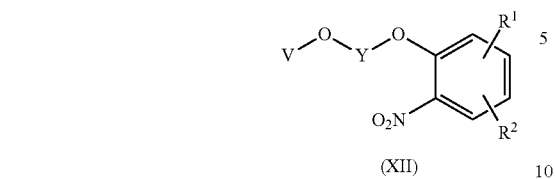

(XII)

↓ Reduction

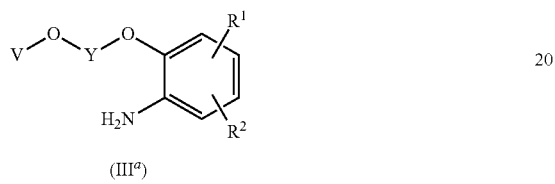

(III$^a$)

X represents a halogen such as for example, Cl, Br and I
V represents a protective group such as for example methylcarbonyl For those compounds where $X^2$ represents —$NR^{12}$— -or —$NR^{12}$—$C_{1-2}$alkyl-, the suitable substituted anilines of formula (III$^b$) are generally prepared from the commercially available 2-nitro-benzaldehydes (XIII) and the amine substituted alcohols (XIV) by reductive amination under standard conditions, for example using NaBH$_4$ and titanium (iv) isopropoxide as reducing agents in ethanol as solvent, yielding in a first step the nitro-benzylamines of formula (XV).

Next the primary free alcohol is protected using art known procedures, for example, using an esterification reaction with acetic anhydride in the presence of pyridine. The thus obtained intermediate of formula (XVI) is subsequently reduced according to standard conditions, for example, using iron/acetic acid to yield the substituted anilines of formula (III$^b$) (Scheme 5).

Scheme 5

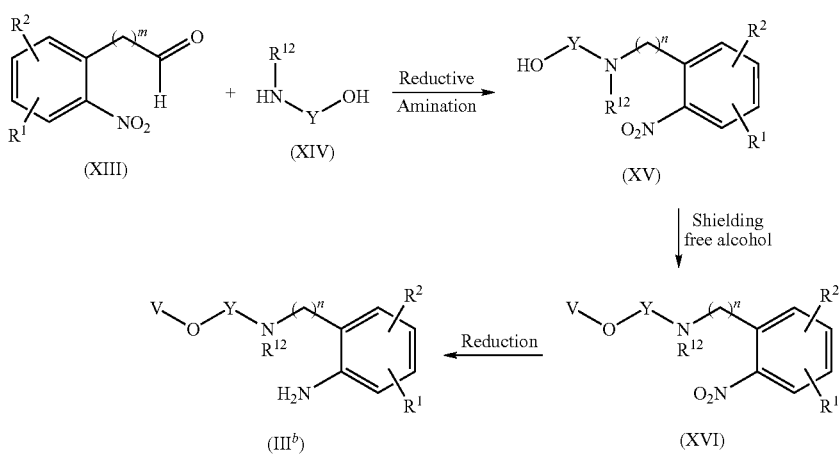

V represents a protective group such as for example methylcarbonyl
m = 0 or 1 and n = 1 or 2

For those compounds where $X^2$ represents O—N═CH—, the suitable substituted anilines of formula (III$^c$) are generally prepared according to reaction scheme 5.

In a first step the known 2-nitro-benzaldehydes (XIII) are converted into the corresponding oxime (XVII) using, for example, the art known condensation reaction with hydroxylamine.

Next said oxime of formula XVII is allowed to react for example, with an halogenated alkylacetate under alkaline conditions, for example using $K_2CO_3$ in DMSO or with a stronger silyl protecting group like TBDMS or TBDPS, and NaH in THF for the reaction conditions, followed by reducing the nitro group, for example, with iron/acetic acid, to provide the suitable substituted aniline of formula (III$^c$).

In a first step the known 2-nitro-benzoic acids (XX) are amidated to the intermediates of formula (XXII) under art known conditions, for example, using a hydroxylated amine of formula (XXI) that is added dropwise to a mixture of (XX) in $CH_2Cl_2$ in the presence of 1,1' carbonylbis-1H-imidazole.

Next the primary free alcohol is protected using art known procedures, for example, using an esterification reaction with acetic anhydride in the presence of pyridine. The thus obtained intermediate of formula (XXIII) is subsequently reduced according to standard conditions, for example, using iron/acetic acid to yield the substituted anilines of formula (III$^d$).

Scheme 6

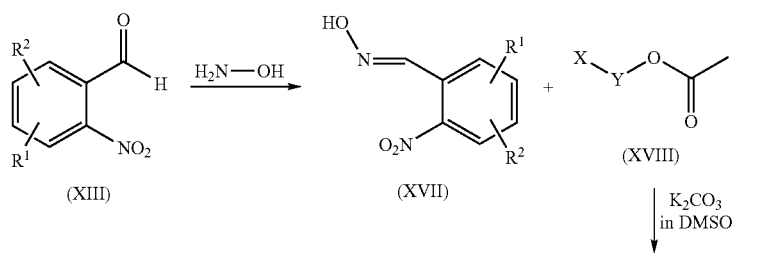

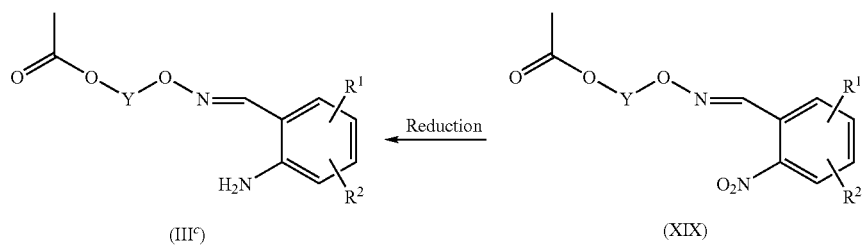

X represents a halogen such as for example Cl, Br or I

For those compounds where $X^2$ represents a direct bond and Y represents $C_{1-6}$alkyl-NH—CO—, the suitable substituted anilines of formula (III$^d$) are generally prepared according to reaction scheme 7.

Scheme 7

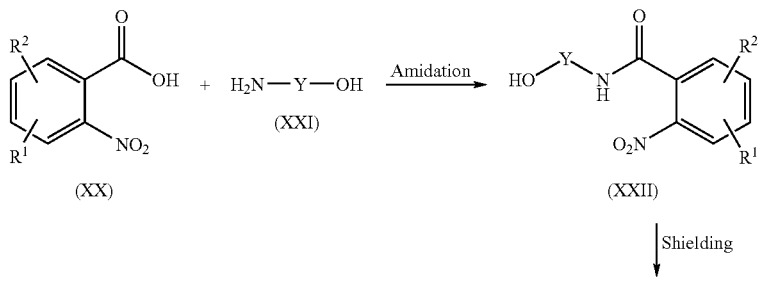

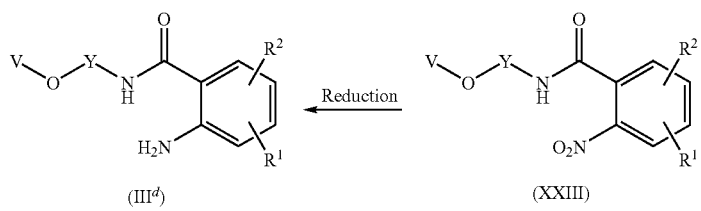

(III$^d$)                            (XXIII)

V represents a protective group such as for example methylcarbonyl

For those compounds where $X^2$ represents a direct bond the suitable substituted anilines of formula (III$^e$) are generally prepared according to reaction scheme 7.

In a first step the known 2-nitro-benzaldehydes (XIII) are alkenated to the intermediates of formula (XXV) under art known conditions, for example, using the Wittig Reaction with the appropriate phosphonium salt of formula (XXIV). Following esterification of the free carboxylic acid under standard conditions for example, using ethanol under acidic conditions, the intermediate of formula (XXVI) are reduced to yield the desired substituted anilines of formula (III$^e$).

Scheme 8

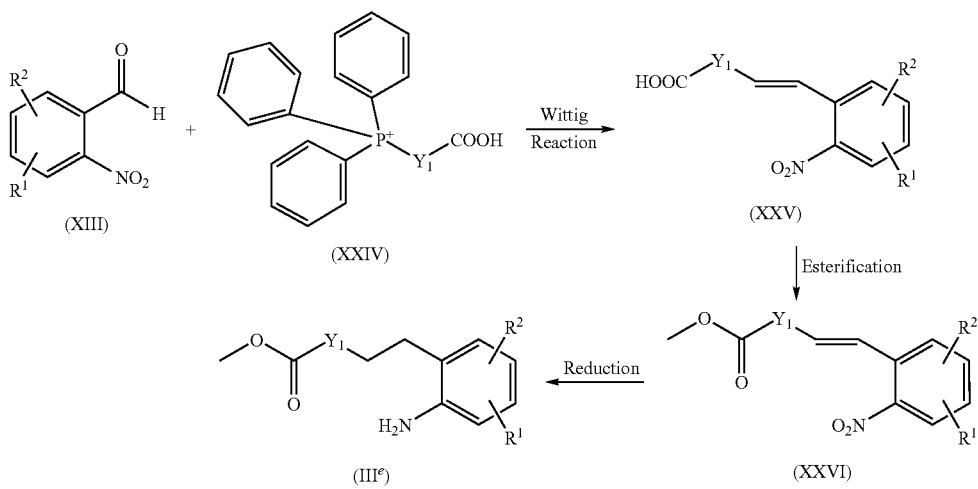

$Y_1$ represents a $C_{1-7}$alkyl

As further exemplified in the experimental part of the description, the group of compounds of formula (I) were —$X^1$— represents —$NR^{11}$— and $a^1$-$a^2$=$a^3$-$a^4$ represents N—CH=N—CH, hereinafter referred to as compounds of formula (I'''), are generally prepared using the following synthesis scheme (Scheme 9). Said compounds may be prepared by coupling the known 8-chloro-2(methylthio)-pyrimido[5,4-d]pyrimidine with 2-aminophenol derivatives of formula (XXVIII), yielding the intermediate compounds of formula (XXIX).

Next, the pyrimido[5,4-d]pyrimidine of formula (XXIX) is aminated using an aminated alcohol (XXX) under art known conditions, followed by ring closure under Mitsunobu conditions to give the target compounds of formula (I''').

Scheme 9

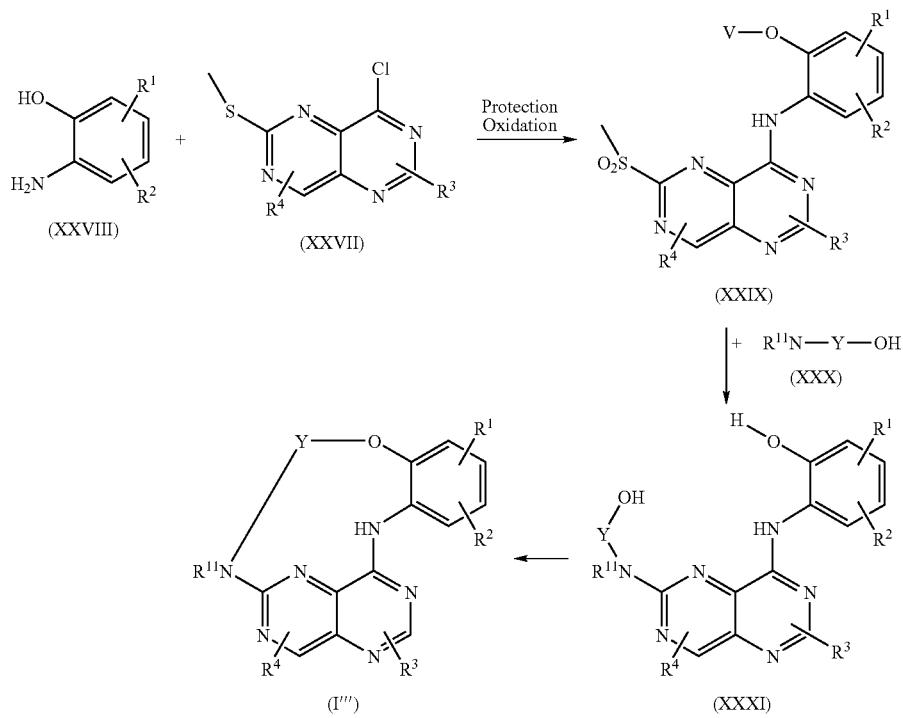

V = Protective group

Alternatively, for those compounds of formula (I) where —$X^1$— represents —$NR^{11}$— and $a^1$-$a^2$=$a^3$-$a^4$ represents N—CH=CH—CH, the compounds are prepared by coupling the known 4,6-dichloro- (XXVII') with 2-aminophenol derivatives of formula (XXVIII), yielding the intermediate compounds of formula (XXIX').

Next, the pyrido[3,2-d]pyrimidine of formula (XXIX') is aminated using an aminated alcohol (XXX) under art known conditions, followed by ring closure under Mitsunobu conditions to give the target compounds of formula (I'''') (Scheme 10).

Scheme 10

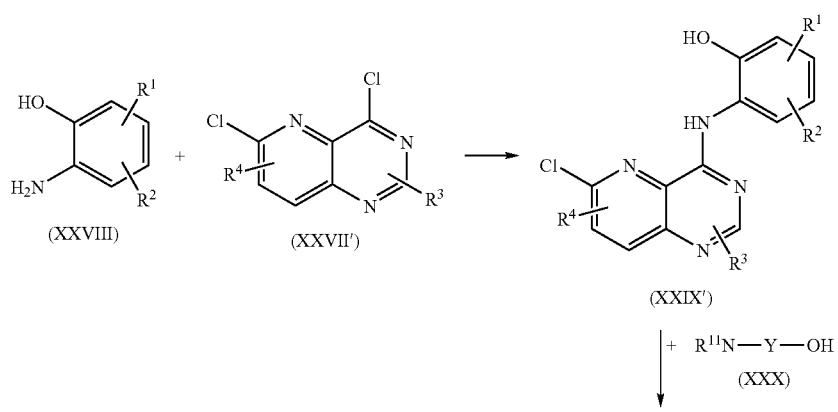

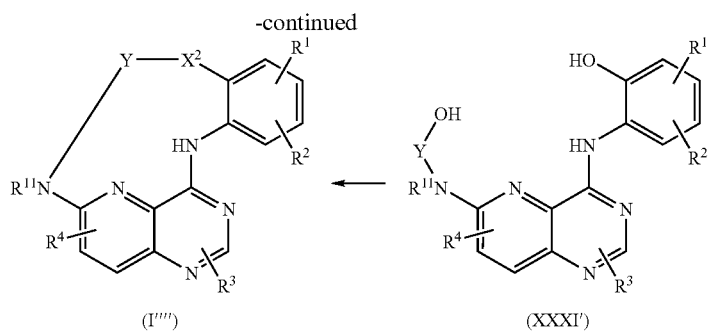

Where necessary or desired, any one or more of the following further steps in any order may be performed:
(i) removing any remaining protecting group(s);
(ii) converting a compound of formula (I) or a protected form thereof into a further compound of formula (I) or a protected form thereof;
(iii) converting a compound of formula (I) or a protected form thereof into a N-oxide, a salt, a quaternary amine or a solvate of a compound of formula (I) or a protected form thereof;
(iv) converting a N-oxide, a salt, a quaternary amine or a solvate of a compound of formula (I) or a protected form thereof into a compound of formula (I) or a protected form thereof;
(v) converting a N-oxide, a salt, a quaternary amine or a solvate of a compound of formula (I) or a protected form thereof into another N-oxide, a pharmaceutically acceptable addition salt a quaternary amine or a solvate of a compound of formula (I) or a protected form thereof;
(vi) where the compound of formula (I) is obtained as a mixture of (R) and (S) enantiomers resolving the mixture to obtain the desired enantiomer.

Compounds of formula (I), N-oxides, addition salts, quaternary amines and stereochemical isomeric forms thereof can be converted into further compounds according to the invention using procedures known in the art.

It will be appreciated by those skilled in the art that in the processes described above the functional groups of intermediate compounds may need to be blocked by protecting groups.

Functional groups, which it is desirable to protect, include hydroxy, amino and carboxylic acid. Suitable protecting groups for hydroxy include trialkylsilyl groups (e.g. tert-butyldimethylsilyl, tert-butyldiphenylsilyl or trimethylsilyl), benzyl and tetrahydropyranyl. Suitable protecting groups for amino include tert-butyloxycarbonyl or benzyloxycarbonyl. Suitable protecting groups for carboxylic acid include $C_{(1-6)}$ alkyl or benzyl esters.

The protection and deprotection of functional groups may take place before or after a reaction step.

Additionally, the N-atoms in compounds of formula (I) can be methylated by art-known methods using $CH_3$—I in a suitable solvent such as, for example 2-propanone, tetrahydrofuran or dimethylformamide.

The compounds of formula (I) can also be converted into each other following art-known procedures of functional group transformation of which some examples are mentioned hereinafter.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with 3-phenyl-2-(phenylsulfonyl)oxaziridine or with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g. counter-current distribution, liquid chromatography and the like.

Some of the compounds of formula (I) and some of the intermediates in the present invention may contain an asymmetric carbon atom. Pure stereochemically isomeric forms of said compounds and said intermediates can be obtained by the application of art-known procedures. For example, diastereoisomers can be separated by physical methods such as selective crystallization or chromatographic techniques, e.g. counter current distribution, liquid chromatography and the like methods. Enantiomers can be obtained from racemic mixtures by first converting said racemic mixtures with suitable resolving agents such as, for example, chiral acids, to mixtures of diastereomeric salts or compounds; then physically separating said mixtures of diastereomeric salts or compounds by, for example, selective crystallization or chromatographic techniques, e.g. liquid chromatography and the like methods; and finally converting said separated diastereomeric salts or compounds into the corresponding enantiomers. Pure stereochemically isomeric forms may also be obtained from the pure stereochemically isomeric forms of the appropriate intermediates and starting materials, provided that the intervening reactions occur stereospecifically.

An alternative manner of separating the enantiomeric forms of the compounds of formula (I) and intermediates involves liquid chromatography, in particular liquid chromatography using a chiral stationary phase.

Some of the intermediates and starting materials as used in the reaction procedures mentioned hereinabove are known compounds and may be commercially available or may be prepared according to art-known procedures. However, in the synthesis of the compounds of formula (I), the present invention further provides the intermediates of formula (III)

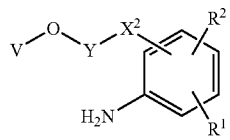

(III)

the pharmaceutically acceptable addition salts and the stereochemically isomeric forms thereof, wherein V represents hydrogen or a protective group preferably selected from the group consisting of methylcarbonyl, t-butyl, methyl, ethyl, benzyl or trialkylsilyl;

Y represents —$C_{3-9}$alkyl-, —$C_{3-9}$alkenyl-, —$C_{1-5}$alkyl-oxy-$C_{1-5}$alkyl-, —$C_{1-5}$alkyl-NR$^{13}$—$C_{1-5}$alkyl-, —$C_{1-5}$alkyl-NR$^{14}$—CO—$C_{1-5}$alkyl-, —$C_{1-5}$alkyl-CO—NR$^{15}$—$C_{1-5}$ alkyl-, —$C_{1-6}$alkyl-CO—NH—, —$C_{1-6}$alkyl-NH—CO—, —$C_{1-7}$alkyl-CO—, $C_{1-6}$alkyl-CO—$C_{1-6}$alkyl;

$X^2$ represents a direct bond, O, —O—$C_{1-2}$alkyl-, CO, —CO—$C_{1-2}$alkyl-, NR$^{12}$, NR$^{12}$—$C_{1-2}$alkyl-, —CH$_2$—, —O—N=CH— or $C_{1-2}$alkyl;

$R^1$ represents hydrogen, cyano, halo, hydroxy, formyl, $C_{1-6}$alkoxy-, $C_{1-6}$alkyl-, $C_{1-6}$alkoxy- substituted with halo, $C_{1-4}$alkyl substituted with one or where possible two or more substituents selected from hydroxy or halo; and $R^2$ represents hydrogen, cyano, halo, hydroxy, hydroxycarbonyl-, Het$^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, Het$^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, Ar$^5$, Ar$^1$-oxy-, dihydroxyborane,
$C_{1-6}$alkoxy- substituted with halo,
$C_{1-4}$alkyl substituted with one or where possible two or more substituents selected from halo, hydroxy or NR$^5$R$^6$,
$C_{1-4}$alkylcarbonyl- wherein said $C_{1-4}$alkyl is optionally substituted with one or where possible two or more substituents selected from hydroxy or $C_{1-4}$alkyl-oxy-;

$R^5$ and $R^6$ are each independently selected from hydrogen or $C_{1-4}$alkyl;

$R^{12}$ represents hydrogen, $C_{1-4}$alkyl, $C_{1-4}$alkyl-oxy-carbonyl-, Het$^{17}$, Het$^{18}$-$C_{1-4}$alkyl-, $C_{2-4}$alkenylcarbonyl- optionally substituted with Het$^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{13}$ represents hydrogen, $C_{1-4}$alkyl, Het$^{13}$, Het$^{14}$-$C_{1-4}$alkyl- or phenyl optionally substituted with one or where possible two or more substituents selected from hydrogen, hydroxy, amino or $C_{1-4}$alkyloxy-;

$R^{14}$ and $R^{15}$ are each independently selected from hydrogen, $C_{1-4}$alkyl, Het$^{15}$-$C_{1-4}$alkyl- or $C_{1-4}$alkyloxy$C_{1-4}$alkyl-;

Het$^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said Het$^1$ is optionally substituted amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-mono- or di($C_{1-4}$alkyl)amino- or amino-carbonyl-;

Het$^{13}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{14}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{15}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl; and Het$^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Het$^{18}$ and Het$^{19}$ each independently represent a heterocycle selected from morpholinyl, pyrrolidinyl, piperazinyl or piperidinyl wherein said Het$^{18}$ and Het$^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

Ar$^1$, Ar$^2$, Ar$^3$, Ar$^4$ and Ar$^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl.

In particular the intermediates of formula (III) wherein one or more of the following restrictions apply:

i) Y represents —$C_{3-9}$alkyl-, —$C_{1-5}$alkyl-oxy-$C_{1-5}$alkyl-, —$C_{1-5}$alkyl-NR$^{13}$—$C_{1-5}$alkyl-, —$C_{1-6}$alkyl-NH—CO—;

ii) $X^2$ represents a direct bond, O, —O—$C_{1-2}$alkyl-, NR$^{12}$, —NR$^{12}$—$C_{1-2}$alkyl-, —CH$_2$—, —O—N=CH— or $C_{1-2}$alkyl;

iii) $R^1$ represents hydrogen, cyano, halo or hydroxy, preferably halo;

iv) $R^2$ represents hydrogen, cyano, halo, hydroxy, hydroxycarbonyl-, $C_{1-4}$alkyloxycarbonyl-, Het$^{16}$-carbonyl-, $C_{1-4}$alkyl-, $C_{2-6}$alkynyl-, Ar$^5$ or Het$^1$;
In a further embodiment $R^2$ represents hydrogen, cyano, halo, hydroxy, $C_{2-6}$ alkynyl- or Het$^1$; in particular $R^2$ represents hydrogen, cyano, halo, hydroxy, or Ar$^5$;

v) $R^{12}$ represents hydrogen, $C_{1-4}$alkyl, or $C_{1-4}$alkyloxycarbonyl;

vi) $R^{13}$ represents Het$^{14}$-$C_{1-4}$alkyl, in particular morpholinyl-$C_{1-4}$alkyl;

vii) Het$^1$ represents thiazolyl optionally substituted with amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl-, mono- or di($C_{1-4}$alkyl)amino- or amino-carbonyl-;

viii) Het$^{16}$ represents a heterocycle selected from piperidinyl or pyrrolidinyl.

It is also an object of the present invention to provide the use of an intermediate of formula (III) in the synthesis of a macrocyclic kinase inhibitor such as for example compound of formula (I).

The compounds of formula (I) and the intermediates of formula (XXXI) of the present invention are useful because they possess pharmacological properties. They can therefore be used as medicines.

Accordingly, in a further aspect this invention concerns the intermediates of formula (XXXI)

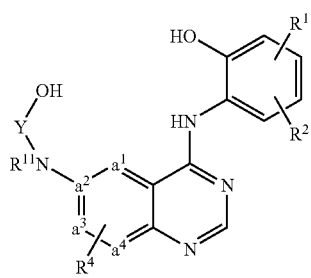

the N-oxide forms, the pharmaceutically acceptable addition salts and the stereochemically isomeric forms thereof, wherein
$a^1$-$a^2$=$a^3$-$a^4$ represents a divalent radical selected from N—CH=CH—CH or N—CH=N—CH;
Y represents —$C_{3-9}$alkyl-, —$C_{1-5}$alkyl-$NR^{13}$—$C_{1-5}$alkyl-, —$C_{1-6}$alkyl-NH—CO— or —CO—NH—$C_{1-6}$alkyl-;
$R^1$ represents hydrogen or halo;
$R^2$ represents hydrogen, cyano, halo, hydroxycarbonyl-, $C_{1-4}$alkyloxycarbonyl-, $Het^{16}$-carbonyl- or $Ar^5$;
$R^4$ represents hydroxy, $C_{1-4}$alkyloxy-, $Ar^4$—$C_{1-4}$alkyloxy or $R^4$ represents $C_{1-4}$alkyloxy substituted with one or where possible two or more substituents selected from $C_{1-4}$alkyloxy- or $Het^2$-;
$R^{11}$ represents hydrogen;
$R^{13}$ represents $Het^{14}$-$C_{1-4}$alkyl, in particular morpholinyl-$C_{1-4}$alkyl;
$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;
In a further embodiment $Het^2$ represents a heterocycle selected from morpholinyl or piperidinyl optionally substituted with $C_{1-4}$alkyl-, preferably methyl;
$Het^{14}$ represents morpholinyl;
$Het^{16}$ represents a heterocycle selected from morpholinyl or pyrrolidinyl;
$Ar^4$ represents phenyl;
$Ar^5$ represents phenyl optionally substituted with cyano; as well as the use of an intermediate of formula (XXXI) in the synthesis of a macrocyclic kinase inhibitor such as for example the compounds of formula (I).

As described in the experimental part hereinafter, the growth inhibitory effect and anti-tumour activity of the present compounds and some of the intermediates has been demonstrated in vitro, in enzymatic assays on the receptor tyrosine kinase EGFR. In an alternative assay, the growth inhibitory effect of the compounds was tested on the ovarian carcinoma cell line SKOV3 using art known cytotoxicity assays such as LIVE/DEAD (Molecular Probes) or MTT.

Accordingly, the present invention provides the compounds of formula (I) and the intermediates of formula (XXXI) and their pharmaceutically acceptable N-oxides, addition salts, quaternary amines and stereochemically isomeric forms for use in therapy. More particular in the treatment or prevention of cell proliferation mediated diseases. The compounds of formula (I), the intermediates of formula (XXXI) and their pharmaceutically acceptable N-oxides, addition salts, quaternary amines and the stereochemically isomeric forms may hereinafter be referred to as compounds according to the invention.

Disorders for which the compounds according to the invention are particularly useful are atherosclerosis, restenosis, cancer and diabetic complications e.g. retinopathy.

In view of the utility of the compounds according to the invention, there is provided a method of treating a cell proliferative disorder such as atherosclerosis, restenosis and cancer, the method comprising administering to an animal in need of such treatment, for example, a mammal including humans, suffering from a cell proliferative disorder, a therapeutically effective amount of a compound according to the present invention.

Said method comprising the systemic or topical administration of an effective amount of a compound according to the invention, to animals, including humans. One skilled in the art will recognize that a therapeutically effective amount of the EGFR inhibitors of the present invention is the amount sufficient to induce the growth inhibitory effect and that this amount varies inter alia, depending on the size, the type of the neoplasia, the concentration of the compound in the therapeutic formulation, and the condition of the patient. Generally, an amount of EGFR inhibitor to be administered as a therapeutic agent for treating cell proliferative disorder such as atherosclerosis, restenosis and cancer, will be determined on a case by case by an attending physician.

Generally, a suitable dose is one that results in a concentration of the EGFR inhibitor at the treatment site in the range of 0.5 nM to 200 µM, and more usually 5 nM to 10 µM. To obtain these treatment concentrations, a patient in need of treatment likely will be administered between 0.01 mg/kg to 300 mg/kg body weight, in particular from 10 mg/kg to 100 mg/kg body weight. As noted above, the above amounts may vary on a case-by-case basis. In these methods of treatment the compounds according to the invention are preferably formulated prior to admission. As described herein below, suitable pharmaceutical formulations are prepared by known procedures using well known and readily available ingredients.

Due to their high degree of selectivity as EGFR inhibitors, the compounds of formula (I) and the intermediates of formula (XXXI) as defined above, are also useful to mark or identify the kinase domain within the receptor tyrosine kinase receptors. To this purpose, the compounds of the present invention can be labelled, in particular by replacing, partially or completely, one or more atoms in the molecule by their radioactive isotopes. Examples of interesting labelled compounds are those compounds having at least one halo which is a radioactive isotope of iodine, bromine or fluorine; or those compounds having at least one $^{11}$C-atom or tritium atom.

One particular group consists of those compounds of formula (I) and intermediates of formula (XXXI) wherein $R^1$ is a radioactive halogen atom. In principle, any compound according to the invention containing a halogen atom is prone for radiolabelling by replacing the halogen atom by a suitable isotope. Suitable halogen radioisotopes to this purpose are radioactive iodides, e.g. $^{122}$I, $^{123}$I, $^{125}$I, $^{131}$I; radioactive bromides, e.g. $^{75}$Br, $^{76}$Br, $^{77}$Br and $^{82}$Br, and radioactive fluorides, e.g. $^{18}$F. The introduction of a radioactive halogen atom can be performed by a suitable exchange reaction or by using any one of the procedures as described hereinabove to prepare halogen derivatives of formula (I).

Another interesting form of radiolabelling is by substituting a carbon atom by a $^{11}$C-atom or the substitution of a hydrogen atom by a tritium atom.

Hence, said radiolabelled compounds according to the invention can be used in a process of specifically marking receptor sites in biological material. Said process comprises the steps of (a) radiolabelling a compound according to the invention, (b) administering this radiolabelled compound to biological material and subsequently (c) detecting the emissions from the radiolabelled compound.

The term biological material is meant to comprise every kind of material which has a biological origin. More in particular this term refers to tissue samples, plasma or body fluids but also to animals, specially warm-blooded animals, or parts of animals such as organs.

When used in in vivo assays, the radiolabelled compounds are administered in an appropriate composition to an animal and the location of said radiolabelled compounds is detected using imaging techniques, such as, for instance, Single Photon Emission Computerized Tomography (SPECT) or Positron Emission Tomography (PET) and the like. In this manner the distribution of the particular receptor sites throughout the body can be detected and organs containing said receptor sites can be visualized by the imaging techniques mentioned hereinabove. This process of imaging an organ by administering a radiolabelled compound of formula (I) and detecting the emissions from the radioactive compound also constitutes a part of the present invention.

In yet a further aspect, the present invention provides the use of the compounds according to the invention in the manufacture of a medicament for treating any of the aforementioned cell proliferative disorders or indications.

The amount of a compound according to the present invention, also referred to here as the active ingredient, which is required to achieve a therapeutical effect will be, of course, vary with the particular compound, the route of administration, the age and condition of the recipient, and the particular disorder or disease being treated. A suitable daily dose would be from 0.01 mg/kg to 300 mg/kg body weight, in particular from 10 mg/kg to 100 mg/kg body weight. A method of treatment may also include administering the active ingredient on a regimen of between one and four intakes per day.

While it is possible for the active ingredient to be administered alone, it is preferable to present it as a pharmaceutical composition. Accordingly, the present invention further provides a pharmaceutical composition comprising a compound according to the present invention, together with a pharmaceutically acceptable carrier or diluent. The carrier or diluent must be "acceptable" in the sense of being compatible with the other ingredients of the composition and not deleterious to the recipients thereof.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). A therapeutically effective amount of the particular compound, in base form or addition salt form, as the active ingredient is combined in intimate admixture with a pharmaceutically acceptable carrier, which may take a wide variety of forms depending on the form of preparation desired for administration. These pharmaceutical compositions are desirably in unitary dosage form suitable, preferably, for systemic administration such as oral, percutaneous or parenteral administration; or topical administration such as via inhalation, a nose spray, eye drops or via a cream, gel, shampoo or the like. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not cause any significant deleterious effects on the skin. Said additives may facilitate the administration to the skin and/or may be helpful for preparing the desired compositions. These compositions may be administered in various ways, e.g., as a transdermal patch, as a spot-on or as an ointment.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Experimental Part

Hereinafter, the term 'ADDP' means 1,1'-(azodicarbonyl)bis-piperidine, 'DMF' means N,N-dimethylformamide, 'THF' means tetrahydrofuran, "DMSO" means dimethyl sulfoxide

A. PREPARATION OF THE INTERMEDIATES

Example A1 a) Preparation of phenol, 4-chloro-2-[(6-chloropyrido[3,2-d]pyrimidin-4-yl)amino]- (Intermediate 1)

A mixture of 4,6-dichloro-pyrido[3,2-d]pyrimidine (0.00255 mol) and 4-chloro-2-aminophenol (0.00446 mol) in isopropanol (30 ml) was stirred at 50° C. for 2 h30, then brought to room temperature and evaporated to dryness. The residue was taken up in ether, filtered and dried, yielding 1 g (100%) of intermediate 1.

b) Preparation of phenol, 4-chloro-2-[[6-[(6-hydroxyhexyl)amino]pyrido[3,2-d]pyrimidin-4-yl]amino]- (Intermediate 2)

A mixture of intermediate 1 (0.00255 mol) and 6-amino-1-hexanol (0.0255 mol) was stirred at 100° C. for 3 hours, then brought to room temperature. The residue was purified by chromatography over silica gel (eluent: DCM/MeOH/

NH₄OH 97/3/0.1; 70-200 μm), yielding 0.71 g (72%) of intermediate 2, melting point 260° C.

Example A2

Preparation of phenol, 4-chloro-2-[[6-[(4-hydroxybutyl)amino]pyrido[3,2-d]pyrimidin-4-yl]amino]- (Intermediate 3)

A mixture of intermediate 1 (0.0013 mol) and 4-amino-1-butanol (0.026 mol) was stirred at 100° C. for 4 hours, then brought to room temperature and hydrolyzed a saturated solution of sodium chloride. The mixture was extracted by DCM, decanted, dried over MgSO₄, filtered, and the solvent was evaporated till dryness. The residue (0.5 g) was purified by column chromatography over silica gel (eluent: DCM/MeOH/NH₄OH 95/5/0.1; 70-200 μm). The residue (81 mg, 17%) was crystallized from acetonitrile and diethyl ether. The precipitate was filtered off and dried, yielding 69 mg (15%) of intermediate 3, melting point 227° C.

Example A3

Preparation of phenol, 4-chloro-2-[[6-[(5-hydroxypentyl)amino]pyrido[3,2-d]pyrimidin-4-yl]amino]- (Intermediate 4)

A mixture of intermediate 1 (0.0013 mol) and 5-amino-1-pentanol (0.0195 mol) was stirred at 100° C. for 4 hours, then brought to room temperature and hydrolyzed a saturated of sodium chloride. The mixture was extracted by DCM, decanted and dried over MgSO₄, filtered, and the solvent was evaporated till dryness. The residue (0.45 g) was purified by column chromatography over silica gel (eluent: DCM/MeOH/NH₄OH 95/5/0.1; 70-200 μm). The residue (66 mg, 14%) was crystallized from acetonitrile and diethyl ether. The precipitate was filtered off and dried, yielding 59 mg (12%) of intermediate 4, melting point 240° C.

Example A4 a) Preparation of phenol, 4-chloro-2-[[6-(methylthio) pyrimido[5,4-d]pyrimidin-4-yl]amino]- (Intermediate 5)

A mixture of 8-chloro-2-(methylthio)-pyrimido[5,4-d]pyrimidine (0.0047 mol) and 2-amino-4-chlorophenol (0.0094 mol) in dioxane (5 ml) was stirred at 80° C. for 1 hour, then cooled to room temperature, the precipitate was filtered off, washed with water and then with diethyl ether and dried in vacuo, yielding 1.2 g (80%) of intermediate 5.

b) Preparation of phenol, 4-chloro-2-[[6-[(6-hydroxyhexyl)amino]pyrimido[5,4-d]pyrimidin-4-yl]amino]- (Intermediate 6)

A mixture of intermediate 1 (0.00172 mol) in 6-amino-1-hexanol (0.0022 mol) was melt at 100° C. after 8 hours. The residue was purified by column chromatography over silica gel (eluent: CH₂Cl₂/CH₃OH/NH₄OH 97/3/0.1; 35-70 μm) yielding 0.170 g of solid. Ether was added. The solid was filtered off and dried in vacuo, yielding 135 mg (20%) of intermediate (6).

Example A5 a) Preparation of pyrido[3,2-d]pyrimidine, 4,6-dichloro- (Intermediate 7)

DMF (3 drops) was added to a mixture of 6-chloro-pyrido [3,2-d]pyrimidin-4(1H)-one [171178-33-9] (0.00275 mol) and thionyl chloride (0.179 mol). The reaction mixture was stirred and refluxed (at 80° C.) for 90 minutes. The solvent was evaporated. Some dichloromethane was added and the solvent was evaporated. The residue was dissolved in dichloromethane. The organic solution was washed with a saturated aqueous K₂CO₃ solution, then dried (MgSO₄), filtered and the solvent was evaporated, yielding 0.49 g (89%) of intermediate (7). (HPLC: 85% P).

b) Preparation of 4-[2-(6-Chloro-pyrido[3,2-d]pyrimidin-4-ylamino)-phenoxy]-butyric acid ethyl ester (Intermediate 8)

Intermediate (7) (0.00245 mol) was dissolved in 2-propanol (20 ml) (not very soluble). 4-(2-Aminophenoxy)butanoic acid ethyl ester (0.00416 mol) was added, followed by addition of N,N-diethylethanamine (0.00490 mol). The reaction mixture was stirred and refluxed overnight. Then, the reaction mixture was cooled to room temperature and the solvent was evaporated. The residue was taken up into diethyl ether. The precipitate was filtered off and dried (pump), yielding 1.48 g of fraction (1) (greenish solid, 92% P by HPLC-MS; presence of some starting material B). This fraction (1) was purified as described below.

The reaction was repeated.

Intermediate (7) (0.0055 mol) was dissolved in 2-propanol (40 ml) (not very soluble). 4-(2-Aminophenoxy)butanoic acid, ethyl ester (0.00935 mol) was added, followed by addition of N,N-diethylethanamine (0.0110 mol). The reaction mixture was stirred and refluxed overnight. Then, the reaction mixture was cooled to room temperature and the solvent was evaporated. The residue was combined with fraction (1) and subjected to flash column chromatography over silica gel (eluent: n-hexane/EtOAc 3/1). The product fractions were collected and the solvent was evaporated, yielding 3.04 g of intermediate (8) (greenish solid in quantitative yield, used in next reaction step without further purification).

c) Preparation of 4-{2-[6-(3-tert-Butoxycarbonylamino-propylamino)-pyrido[3,2-d]pyrimidin-4-ylamino]-phenoxy}-butyric acid ethyl ester (Intermediate 9)

Intermediate (8) (0.00026 mol) and (3-aminopropyl)carbamic acid 1,1-dimethylethyl ester (0.00288 mol) were mixed for 3 hours at 100° C. in a closed reactor, yielding fraction (1) (57% P by HPLC+35% of the amide).

This fraction (1) was purified as described below.

The reaction was repeated.

Intermediate (8) (0.00026 mol) and (3-aminopropyl)carbamic acid 1,1-dimethylethyl ester (0.00288 mol) were mixed for 2.5 hours at 100° C. in an open reaction flask (not in a closed reactor as described above). The mixture was combined with fraction (1). Purified by flash column chromatography over silica gel (eluent: n-hexane/EtOAc 3/1). The product fractions were collected and the solvent was evaporated, yielding intermediate (9) (HPLC: 92% P).

d) Preparation of 4-{2-[6-(3-Amino-propylamino)-pyrido[3,2-d]pyrimidin-4-ylamino]-phenoxy}-butyric acid ethyl ester (Intermediate 10)

Intermediate (9) ((0.00019 mol) was dissolved in dichloromethane (4.00 ml). Trifluoroacetic acid (0.05192 mol) was added and the reaction mixture was stirred for 2 hours at room temperature. The solvent and remaining acid were evaporated in the rotary evaporator. The resultant residue (oil) was dried (high-vacuum pump), yielding intermediate (10) (HPLC: 93% P; quantitative yield; used in next reaction step, without further purification).

e) Preparation of 4-{2-[6-(3-Amino-propylamino)-pyrido[3,2-d]pyrimidin-4-ylamino]-phenoxy}-butyric acid (Intermediate 11)

Intermediate (10) (0.00019 mol; 1 equiv) was dissolved in tetrahydrofuran (8.00 ml). Water (1.00 ml) was added. Lithium hydroxide monohydrate (0.0019 mol) was added as a solid. More Lithium hydroxide monohydrate was added until a basic pH was reached (until then it was acidic because of $CF_3COOH$ remainders). The reaction mixture was stirred for 2 days at 65° C. The solvent was evaporated in the rotary evaporator, yielding intermediate (11). (HPLC: 78% P; quantitative yield; used in next reaction step, without further purification).

Example A6 a) Preparation of 4-chloro-6-fluoro-pyrido[3,4-d]pyrimidine, (Intermediate 12)

DMF (5 drops) was added to a mixture of 6-Fluoro-3H-pyrido[3,4-d]pyrimidin-4-one (0.00605 mol) and thionyl chloride (0.39 mol). The reaction mixture was stirred and refluxed (at 80° C.) for 7 hours. The solvent was evaporated, yielding 1.254 g of intermediate (12) (impure quantitative yield; used in next reaction step, without further purification).

b) Preparation of 4-[2-(6-Fluoro-pyrido[3,4-d]pyrimidin-4-ylamino)-phenoxy]-butyric acid ethyl ester (Intermediate 13)

Intermediate (12) (0.00605 mol) was dissolved in 2-propanol (40 ml). 4-(2-aminophenoxy)-butanoic acid, ethyl ester [112290-16-1].hydrochloride (0.01028 mol) was added, followed by addition of N,N-diethylethanamine (0.01210 mol). The reaction mixture was stirred and refluxed overnight. Then, the reaction mixture was cooled to room temperature and the solvent was evaporated. The residue was purified by flash column chromatography over silica gel (eluent: n-hexane/EtOAc 3/1). The product fractions were collected and the solvent was evaporated, yielding 0.922 g of intermediate (13) (41% yield over two steps; yellowish solid; 97% P by HPLC).

c) Preparation of 4-{2-[6-(3-tert-Butoxycarbonylamino-propylamino)-pyrido[3,4-d]pyrimidin-4-ylamino]-phenoxy}-butyric acid ethyl ester (Intermediate 14)

Intermediate (13) (0.00027 mol) was dissolved in DMSO (q.s.), in a reactor. (3-Aminopropyl)carbamic acid 1,1-dimethylethyl ester [75178-96-0] (0.07 ml) and N-ethyl-N-(1-methylethyl)-2-propanamine [7087-68-5] (0.10 ml) were added. The reactor was closed and the mixture was heated for 7 days at 80° C. The reaction mixture was poured out into water and the product was extracted three times with dichloromethane. The combined organic layers were dried ($MgSO_4$), filtered and the solvent was evaporated, yielding fraction 1 of intermediate (14).

Two other fractions of Intermediate 14 were prepared as follows:

Intermediate (13) (0.00027 mol) and (3-aminopropyl)carbamic acid 1,1-dimethylethyl ester [75178-96-0] (0.00299 mol) were mixed in a (closed) reactor and heated at 100° C. for 3 hours, yielding fraction 2 of intermediate (14).

Intermediate (13) (0.00008 mol) and (3-aminopropyl)carbamic acid 1,1-dimethylethyl ester [75178-96-0] (0.0009 mol) were mixed in an open reaction flask and heated at 80° C. for 3 days, yielding fraction 3 of intermediate (14)

Fraction 1, 2 and 3 of intermediate 14 were combined and purified by flash column chromatography over silica gel.

Intermediate 14 was also prepared as follows:
Intermediate (13) (0.00027 mol) was dissolved in DMF (3 ml). (3-Aminopropyl)carbamic acid 1,1-dimethylethyl ester [75178-96-0] (0.00040 mol) and cesium carbonate (0.00135 mol) were added and the reaction mixture was stirred for 4 hours at 100° C., then overnight at 115° C. Excess of cesium carbonate was removed by filtration. The filtrate was evaporated, yielding intermediate (14).

d) Preparation of 4-{2-[6-(3-Amino-propylamino)-pyrido[3,4-d]pyrimidin-4-ylamino]-phenoxy}-butyric acid ethyl ester (Intermediate 15)

Intermediate (14) (0.00055 mol) was dissolved in dichloromethane (11.00 ml). Trifluoroacetic acid (0.143 mol) was added and the reaction mixture was stirred for 2 hours at room temperature. The solvent and remaining acid were evaporated in the rotary evaporator. The resultant residue (oil) was dried (high-vacuum pump), yielding intermediate (15) (HPLC: 91% P; quantitative yield; used in next reaction step, without further purification).

e) Preparation of 4-{2-[6-(3-Amino-propylamino)-pyrido[3,4-d]pyrimidin-4-ylamino]-phenoxy}-butyric acid (Intermediate 16)

Intermediate (15) (0.00055 mol) was dissolved in tetrahydrofuran (16.00 ml). Water (2.00 ml) was added. Lithium hydroxide.monohydrate (0.0055 mol) was added as a solid. More lithium hydroxide.monohydrate was added until a basic pH was reached (until then it was acidic because of $CF_3COOH$ remainders). The reaction mixture was stirred overnight at 65° C. The solvent was evaporated in the rotary evaporator, yielding intermediate (16) (HPLC: 88% P; quantitative yield; used in next reaction step, without further purification).

Example A7 a) Preparation of Allyl-(4-chloro-5-fluoro-2-nitrobenzyl)-methyl-amine (Intermediate 17)

N-methyl-2-propen-1-amine (1.1 equiv) was added to a solution of 4-chloro-5-fluoro-2-nitro-benzaldehyde (1 equiv) in 1,2-dichloroethane (207 ml), then $MgSO_4$ (2 spoons) was added and the obtained solution was stirred for 2 hours at room temperature. $NaBH(OAc)_3$ (3 equiv) was added in 5 portions (one portion per hour) and the reaction mixture was washed with $K_2CO_3$. After extraction with $CH_2Cl_2$, the layers were separated. The organic layer was dried over MgSO₄, filtered and evaporated, to afford intermediate (17).

b) Preparation of 2-[(Allyl-methyl-amino)-methyl]-5-chloro-4-fluoro-phenylamine (Intermediate 18)

A solution of the nitro derivative intermediate (17) (1 equiv) in a solution of H₂O (120 ml) and NH₄Cl (5 equiv) at room temperature was dissolved in Toluene (120 ml), then iron powder (5 equiv) was slowly added and the reaction mixture was stirred and refluxed at 105° C. The obtained crude was purified by Flash Chromatography. The desired product fractions were collected and the solvent was evaporated, to afford 4.8 g of intermediate (18).

c) Preparation of {2-[(Allyl-methyl-amino)-methyl]-5-chloro-4-fluoro-phenyl}-(6-chloro-pyrido[3,2-d]pyrimidin-4-yl)-amine (Intermediate 19)

Triethylamine (3 equiv) was added to a solution of 4,6-dichloro-pyrido[3,2-d]pyrimidine (1 equiv.) in acetonitrile (dried over Al₂CO₃) (9 ml). HCl evolved and the reaction mixture was purged with N₂ for 10 to 15 minutes. Intermediate (18) was added (1.7 equiv.) and then the reaction mixture was stirred and refluxed for 5 hours. After cooling to room temperature, a slightly yellow solid precipitated from the mixture. The product was collected and dried under high vacuum, to yield desired product. EtOAc was added to the mother layer and then a white solid precipitated. After filtration, the filtrate was concentrated and the obtained concentrate was purified by Flash chromatography over silica gel (eluent: Hexane/EtOAc 9/1). The desired fractions were collected and the solvent was evaporated, to yield desired product. Both fractions of desired product were collected, to yield 0.750 g intermediate (19).

d) Preparation of $N^6$-Allyl-$N^4$-{2-[(allyl-methyl-amino)-methyl]-5-chloro-4-fluoro-phenyl}-pyrido[3,2-d]pyrimidine-4,6-diamine (Intermediate 20)

A solution of intermediate (19) (1 equiv) in 2-propenylamine (9.8 equiv) was heated overnight in a sealed tube at 100° C., then the resulting solution was concentrated and dried under high vacuum, to obtain 0.487 g (115%) of a semi solid that was redissolved in CH₂Cl₂. The solution was then filtered and the filtrate was concentrated again, to afford 0.412 g (100%) of intermediate (20).

e) Preparation of 4,6-ethanediylidenepyrimido[4,5-b][1,4,6,11]benzotetraazacyclotetradecine, 16-chloro-15-fluoro-7,8,11,12,13,18-hexahydro-12-methyl-, (9E)- (Intermediate 21)

A mixture of intermediate (20) and Grubbs's Catalyst second generation (0.2 equiv) in CH₂Cl₂ (7 ml) was stirred and refluxed for 6 hours, then the reaction mixture was stirred for 72 hours at room temperature and refluxed again. An extra amount of B (20%) was added and then the resulting mixture was stirred and refluxed again for 6 hours. Again extra B (20%) was added and the mixture was refluxed again overnight. After concentration, the obtained residue was purified by Flash chromatography over silica gel (eluent: Acetate/Hexane 1/1). The desired fraction were collected and the solvent was evaporated, to yield 0.025 g (38%) of pure intermediate (21).

B. PREPARATION OF THE COMPOUNDS

Example B1

Preparation of 7H,19H-4,6-ethanediylidenepyrimido[4,5-b][13,1,4,6]benzoxatriazacyclopentadecine, 17-chloro-8,9,10,11,12,13-hexahydro- (compound 1)

In two separate dropping funnels, a solution of tributylphosphine (0.00268 mol) in THF (20 ml) and a solution of ADDP (0.00155 mol) in THF (20 ml) were slowly simultaneously added to a solution of intermediate 2 (0.00103 mol) in THF (20 ml) and DMF (2 m) chilled at 0° C. under an atmosphere of nitrogen. The reaction mixture was stirred for 4 hours at room temperature, poured out into a 1N solution of aqueous hydrochloric acid and after 1 hour, the mixture was diluted with DCM. The precipitate was filtered off, the organic phase was partitioned with a 10% aqueous solution of potassium carbonate, dried (MgSO₄) and concentrated in vacuo. The solid residue was sonicated in hot isopropanol, filtered off, washed with dry ether and dried in vacuo, yielding 0.16 g (44%) of compound (1).

Example B2

Preparation of 6,4-(nitrilometheno)pyrimido[4,5-b][13,1,4,6]benzoxatriazacyclopentadecine, 17-chloro-7,8,9,10,11,12,13,19-octahydro- (Compound 2)

In two separate dropping funnels, a solution of ADDP (0.00102 mol) in THF (2 ml) and a solution of tributylphosphine (0.00177 mol) in THF (2 ml) were slowly simultaneously added to a solution of intermediate 6 (0.000681 mol) in THF (10 ml) and DMF (1.4 ml), and stirred at room temperature for 18 hours. Then, a solution of ADDP (0.000340 mol) in THF (0.7 mL) and a solution of tributylphosphine (0.000592 mol) in THF (0.7 mL) were simultaneously added at room temperature for 2 hours. The mixture was hydrolyzed and the precipitate was filtered off, wash with water then with isopropanol and the diethyl ether, and dried in vacuo, yielding 0.124 g (49%) of compound (2), melting point >260° C.

Example B3

Preparation of 7H,21H-4,6-ethanediylidenepyrimido[4,5-b][15,1,4,6,10]benzoxatetranzacycloheptadecin-12(13H)-one, 8,9,10,11,14,15-hexahydro- (Compound 3)

1-[bis(dimethylamino)methylene]-3-oxide-1H-benzotriazolium, hexafluorophosphate(1-) [94790-37-1] (0.00057 mol) was dissolved in DMF (20 ml) and stirred at room temperature. Intermediate (11) (0.00019 mol) was dissolved in DMF (10 ml) and N-ethyl-N-(1-methylethyl)-2-propanamine (0.00114 mol) was added. This solution was added slowly over a 2 hours period to the first solution. The light-green solution was stirred overnight at room temperature. The solvent (DMF) was evaporated. The residue was purified by flash column chromatography, yielding compound (3).

| Compounds that are prepared according to Example B3 | |
|---|---|
| 4,6-ethanediylidenepyrimido[4,5-b][1,4,6,10,13]benzopentaazacyclohexadecin-12(7H)-one, 18-chloro-17-fluoro-8,9,10,11,13,14,15,20-octahydro- | Compound 6 |
| -4,6-ethanediylidenepyrimido[4,5-b]pyrrolo[2,1- | Com- |

-continued

| Compounds that are prepared according to Example B3 | |
|---|---|
| l][1,4,6,10,13]benzopentaazacyclohexadecin-12(7H)-one, 20-chloro-19-fluoro-8,9,10,11,12a,13,14,15,17,22-decahydro-4,6-ethanediylidenepyrimido[4,5-b][1,4,6,10,13]benzopentaazacyclohexadecin-12(7H)-one, 18-chloro-17-fluoro-8,9,10,11,13,14,15,20-octahydro-14-methyl-4,6-ethanediylidene-11H-pyrimido[4,5-b][1,4,6,9,12]benzopentaazacyclopentadecin-11-one, 17-chloro-16-fluoro-7,8,9,10,12,13,14,19-octahydro-13-methyl-4,6-ethanediylidenepyrimido[4,5-b][1,4,6,10,13]benzopentaazacyclohexadecin-12(7H)-one, 18-chloro-17-fluoro-8,9,10,11,13,14,15,20-octahydro-13-(2-4,6-ethanediylidenepyrimido[4,5-b][1,4,6,10,13]benzopentaazacyclooctadecin-15(16H)-one, 20-bromo-7,8,9,10,11,12,13,14,17,22-decahydro-4,6-ethanediylidenepyrimido[4,5-b][1,4,6,10,14]benzopentaazacyclooctadecin-16(7H)-one, 20-chloro-8,9,10,11,12,13,14,15,17,22-decahydro-4,6-ethanediylidene-7H-pyrimido[4,5-b][1,4,6,10,14]benzopentaazacyclononadecin-16(17H)-one, 21-chloro-8,9,10,11,12,13,14,15,18,23-decahydro-4,6-ethanediylidenepyrimido[4,5-b][1,4,6,10,13]benzopentaazacyclooctadecin-15(16H)-one, 20-chloro-7,8,9,10,11,12,13,14,17,22-decahydro- | Compound 7<br>Compound 8<br>Compound 9<br>Compound 10<br>Compound 11<br>Compound 12<br>Compound 13<br>Compound 14 |

Example B4

Preparation of 7H,21H-6,4-(nitrilometheno)pyrimido [5,4-m][1,6,10,15]benzoxa-triazacycloheptadecin-12 (13H)-one, 8,9,10,11,14,15-hexahydro- (Compound 4)

1-[bis(dimethylamino)methylene]-3-oxide-1H-benzotriazolium, hexafluoro-phosphate(1-) [94790-37-1] (0.00165 mol) was dissolved in DMF (40 ml) and stirred at room temperature. Intermediate (16) (0.00055 mol) was dissolved in DMF (20 ml) and N-ethyl-N-(1-methylethyl)-2-propanamine (0.0033 mol) was added. This solution was added slowly over a 2 hours period to the first solution. The light-green solution was stirred overnight at room temperature. The solvent (DMF) was evaporated, yielding compound (4).

| Compounds that are prepared according to Example B4 | |
|---|---|
| 6,4-(nitrilometheno)pyrimido[4,5-b][1,6,10,13]benzotetraazacyclohexadecin-12(7H)-one, 18-chloro-17-fluoro-8,9,10,11,13,14,15,20-octahydro--6,4-(nitrilometheno)pyrimido[4,5-b]pyrrolo[2,1-l][1,6,10,13]benzotetraazacyclohexadecin-12(7H)-one, 20-chloro-19-fluoro-8,9,10,11,12a,13,14,15,17,22-decahydro--6,4-(nitrilometheno)pyrimido[4,5-b][1,6,10,13]benzotetraazacyclohexadecin-12(7H)-one, 18-chloro-17-fluoro-8,9,10,11,13,14,15,20-octahydro-14-methyl-6,4-(nitrilometheno)-11H-pyrimido[4,5-b][1,6,9,12]benzotetraazacyclopentadecin-11-one, 17-chloro-16-fluoro-7,8,9,10,12,13,14,19-octahydro-13-methyl-6,4-(nitrilometheno)pyrimido[4,5-b][1,6,10,13]benzotetraazacyclohexadecin-12(7H)-one, 18-chloro-17-fluoro-8,9,10,11,13,14,15,20-octahydro-13-(2-methylpropyl)-6,4-(nitrilometheno)pyrimido[4,5-b][1,6,10,13]benzotetraazacyclooctadecin-15(16H)-one, 20-bromo-7,8,9,10,11,12,13,14,17,22-decahydro-6,4-(nitrilometheno)pyrimido[4,5-b][1,6,10,14]benzotetraazacyclooctadecin-16(7H)-one, 20-chloro-8,9,10,11,12,13,14,15,17,22-decahydro-6,4-(nitrilometheno)-7H-pyrimido[4,5-b][1,6,10,14]benzotetraazacyclononadecin-16(17H)-one, 21-chloro-8,9,10,11,12,13,14,15,18,23-decahydro-6,4-(nitrilometheno)pyrimido[4,5-b][1,6,10,13]benzotetraazacyclooctadecin-15(16H)-one, 20-chloro-7,8,9,10,11,12,13,14,17,22-decahydro- | Compound 15<br>Compound 16<br>Compound 17<br>Compound 18<br>Compound 19<br>Compound 20<br>Compound 21<br>Compound 22<br>Compound 23 |

All other compounds can be prepared according to these procedures with the remark that the cpds with Y being $C_{1-5}$ alkyl and $X^2/X^1$ NH are cyclized under ring closing metathesis conditions using second generation Grubbs catalysts of the dienes (see example B5 hereinafter)

Example B5

Preparation of 4,6-ethanediylidenepyrimido[4,5-b] [1,4,6,11]benzotetraazacyclotetradecine, 16-chloro-15-fluoro-7,8,9,10,11,12,13,18-octahydro-12-methyl- (Compound 5)

Intermediate (21) (1 equiv) was dissolved in a methanol/dioxane mixture (4/1), then catalyst Pt/C (0.3 equiv) was added and the reaction mixture was stirred for 4 hours under $H_2$ atmosphere. The resulting mixture was filtered over a short celite pad and the filtrate was concentrated to dryness. The obtained residue was dried under high vacuum, to afford 0.029 g (60%) of pure compound (5).

Compound Identification

The compounds were identified by LC/MS using a gradient elution system on a reversed phase HPLC. The compounds are identified by their specific retention time and their protonated molecular ion MH⁺ peak. The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 μm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 6.5 minutes, to 100% B in 1 minute, 100% B for 1 minute and reequilibrate with 100% A for 1.5 minutes. An injection volume of 10 μL was used.

Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionization mode and 20 V for negative ionization mode. Data acquisition was performed with a Waters-Micromass MassLynx-Openlynx data system.

TABLE retention time (RT in minutes) and molecular weight as the MH⁺

| Compound No. | Rt | MH+ |
|---|---|---|
| 9 | 6.57 | 416 |
| 5 | 8.78 | 387 |
| 7 | 6.87 | 456 |
| 11 | 5.44 | 470 |
| 14 | 5.42 | 426 |
| Int. 20 | 8.62 | 413 |
| Int. 21 | 8.06 | 387 |
| 3 | 6.08 | 379 |
| 4 | 5.77 | 379 |

C. PHARMACOLOGICAL EXAMPLES

Example C.1

In vitro Inhibition of EGFR

The in vitro inhibition of EGFR was assessed using either the Flash Plate technology or the glass-fiber filter technology as described by Davies, S. P. et al., Biochem J. (2000), 351; p. 95-105. The Flash Plate technology is generally described by B. A. Brown et al. in High Throughput Screening (1997), p. 317-328. Editor(s): Devlin, John P. Publisher: Dekker, New York, N.Y.

In the Flash Plate EGFR kinase reaction assay, a kinase substrate consisting of biotinylated poly(L-glutamic acid-L-tyrosine) (poly(GT)biotin), is incubated with the aforementioned protein in the presence of ($^{33}$P) radiolabeled ATP. ($^{33}$P) phosphorylation of the substrate is subsequently measured as light energy emitted using a streptavidin-coated Flash Plate (PerkinElmer Life Sciences) by trapping and quantifying the binding of the biotin tagged and radiolabeled substrate.

DETAILED DESCRIPTION

The EGFR kinase reaction is performed at 30° C. for 60 minutes in a 96-well microtiter FlashPlate (PerkinElmer Life Sciences). For each of the tested compounds a full dose response $1.10^{-6}$M to $1.10^{-10}$M has been performed. IRESSA® and Tarceva™ (erlotinib) were used as reference compounds. The 100 μl reaction volume contains 54.5 mM TrisHCl pH 8.0, 10 mM MgCl$_2$, 100 μM Na$_3$VO$_4$, 5.0 μM unlabeled ATP, 1 mM DTT, 0.009% BSA, 0.8 μCi AT$^{33}$P, 0.35 μg/well poly(GT)biotin and 0.5 μg EGFR-kinase domain/well.

The reaction is stopped by aspirating the reaction mixture and washing the plate 3× with 200 μl wash/stop buffer (PBS+ 100 mM EDTA). After the final wash step 200 μl of wash/stop buffer was added to each well and the amount of phosphorylated ($^{33}$P) Poly(GT)biotin determined by counting (30 sec/well) in a microtiterplate scintillation counter.

In the glass-fiber filter technology EGFR kinase reaction assay, a kinase substrate consisting of poly(L-glutamic acid-L-tyrosine) (poly(GT)), is incubated with the aforementioned protein in the presence of ($^{33}$P) radiolabeled ATP. ($^{33}$P) Phosporylation of the substrate is subsequently measured as radioactivity bound on a glassfiber-filter.

Detailed Description

The EGFR kinase reaction is performed at 25° C. for 10 minutes in a 96-well microtiterplate. For each of the tested compounds a full dose response $1.10^{-6}$M to $1.10^{-10}$M has been performed. IRESSA® and Tarceva™ (erlotinib) were used as reference compounds. The 25 μl reaction volume contains 60 mM TrisHCl pH 7.5, 3 mM MgCl$_2$, 3 mM Mn Cl$_2$, 3 μM Na$_3$VO$_4$, 50 μg/ml PEG20000, 5.0 μM unlabeled ATP, 1 mM DTT, 0.1 μCi AT$^{33}$P, 62.5 ng/well poly(GT) and 0.5 μg EGFR-kinase domain/well.

The reaction is stopped by adding 5 μl of a 3% phosphoric acid solution. 10 μl of the reaction mixture is then spotted onto a Filtermat A filter (Wallac) and washed 3 times for 5 min. in 75 mM phosphoric acid and 1 time for 5 min. in methanol prior to drying and quantification on the Typhoon (Amersham) using a LE phosphorage storage screen.

Example C.2

Serum Starved Proliferation Assay on the Ovarian Carcinoma SKOV3 Cells

The ovarian carcinoma cell line (SKOV3) was used in an epidermal growth factor stimulated cell proliferation assay, to assess the inhibitory effect of the compounds on EGF in whole cells.

In a first step the SKOV3 cells were incubated for 24 hours in the presence of 10% FCS serum. In the second step the cells were incubated with the compounds to be tested in a serum free condition (37° C. and 5% (v/v) CO$_2$) and subsequently stimulated for 72 hours with EGF at a final concentration of 100 ng/ml. The effect of the compounds on the EGF stimulation was finally assessed in a standard MTT cell viability assay.

The following table provides the pIC50 values of the compounds according to the invention, obtained using the above mentioned kinase assays.

| Compound number | In vitro kinase activity assay.(C1): IC50 in nM | SKOV3 cell (C2): IC50 in μM | Intermediate number | In vitro kinase activity assay.(C1): IC50 in nM | SKOV3 cell (C2): IC50 in μM |
| --- | --- | --- | --- | --- | --- |
| 2 | 8.5 | <5.0 | 2 | 8.2 | 5.5 |
| 1 | 8.3 | 6.23 | 3 | 8.4 | 6.1 |
|   |     |      | 4 | 8.3 | 5.8 |
|   |     |      | 6 | 8.4 | 6.0 |

D. COMPOSITION EXAMPLES

The following formulations exemplify typical pharmaceutical compositions suitable for systemic administration to animal and human subjects in accordance with the present invention.

"Active ingredient" (A.I.) as used throughout these examples relates to a compound of formula (I), (XXXI) or a pharmaceutically acceptable addition salt thereof.

Example D. 1

Film-Coated Tablets

Preparation of Tablet Core

A mixture of A.I. (100 g), lactose (570 g) and starch (200 g) was mixed well and thereafter humidified with a solution of sodium dodecyl sulfate (5 g) and polyvinyl-pyrrolidone (10 g) in about 200 ml of water. The wet powder mixture was sieved, dried and sieved again. Then there was added microcrystalline cellulose (100 g) and hydrogenated vegetable oil (15 g). The whole was mixed well and compressed into tablets, giving 10.000 tablets, each comprising 10 mg of the active ingredient.

Coating

To a solution of methyl cellulose (10 g) in denaturated ethanol (75 ml) there was added a solution of ethyl cellulose (5 g) in CH$_2$Cl$_2$ (150 ml). Then there were added CH$_2$Cl$_2$ (75 ml) and 1,2,3-propanetriol (2.5 ml). Polyethylene glycol (10 g) was molten and dissolved in dichloromethane (75 ml). The latter solution was added to the former and then there were added magnesium octadecanoate (2.5 g), polyvinyl-pyrrolidone (5 g) and concentrated color suspension (30 ml) and the

The invention claimed is:
1. A compound having the formula

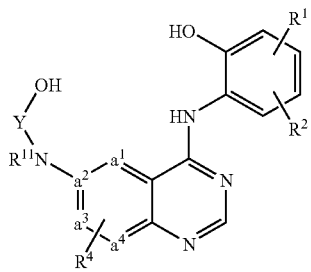

(XXXI)

the N-oxide forms, the pharmaceutically acceptable addition salts and the stereochemically isomeric forms thereof, wherein
$a^1$-$a^2$=$a^3$-$a^4$ represents a divalent radical selected from N—CH=CH—CH or N—CH=N—CH;
Y represents —$C_{3-9}$alkyl-, —$C_{1-5}$alkyl-$NR^{13}$—$C_{1-5}$alkyl-, —$C_{1-6}$alkyl-NH—CO— or —CO—NH—$C_{1-6}$alkyl-;
$R^1$ represents hydrogen or halo;
$R^2$ represents hydrogen, cyano, halo, hydroxycarbonyl-, $C_{1-4}$alkyloxycarbonyl-, $Het^{16}$-carbonyl- or $Ar^5$;
$R^4$ represents hydroxy, $C_{1-4}$alkyloxy-, $Ar^4$—$C_{1-4}$alkyloxy or $R^4$ represents $C_{1-4}$alkyloxy substituted with one or where possible two or more substituents selected from $C_{1-4}$alkyloxy- or $Het^2$-;
$R^{11}$ represents hydrogen;
$R^{13}$ represents $Het^{14}$-$C_{1-4}$alkyl;
$Het^2$ represents a heterocycle selected from morpholinyl, piperazinyl, piperidinyl or pyrrolidinyl wherein said $Het^2$ is optionally substituted with one or where possible two or more substituents selected from hydroxy, amino or $C_{1-4}$alkyl-;
$Het^{14}$ represents morpholinyl;
$Het^{16}$ represents a heterocycle selected from morpholinyl or pyrrolidinyl;
$Ar^4$ represents phenyl;
$Ar^5$ represents phenyl optionally substituted with cyano.

2. A process for preparing a compound of formula (I)

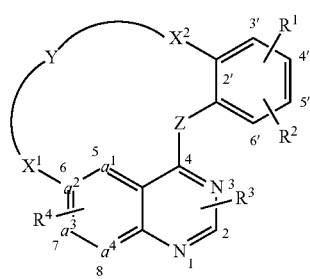

(I)

the N-oxide forms, the pharmaceutically acceptable addition salts and the stereochemically isomeric forms thereof, wherein
$a^1$-$a^2$=$a^3$-$a^4$ represents a divalent radical selected from N—CH=CH—CH, N—CH=N—CH or CH—CH=N—CH;
Z represents O, NH or S;
Y represents —$C_{3-9}$alkyl-, —$C_{3-9}$alkenyl-, —$C_{1-5}$alkyl-oxy-$C_{1-5}$alkyl-, —$C_{1-5}$alkyl-$NR^{13}$—$C_{1-5}$alkyl-, —$C_{1-5}$alkyl-$NR^{14}$—CO—$C_{1-5}$alkyl-, —$C_{1-5}$alkyl-CO—$NR^{15}$—$C_{1-5}$alkyl-, —$C_{1-5}$alkyl-CO—NH—, —$C_{1-6}$alkyl-NH—CO—, —CO—NH—$C_{1-6}$alkyl-, —NH—CO—$C_{1-6}$alkyl-, —CO—$C_{1-7}$alkyl-, —$C_{1-7}$alkyl-CO—, $C_{1-6}$alkyl-CO—$C_{1-6}$alkyl;
$X^1$ represents a direct bond, O, —O—$C_{1-2}$alkyl-, CO, —CO—$C_{1-2}$alkyl-, $NR^{11}$, —$NR^{11}$—$C_{1-2}$alkyl-, $NR^{16}$—CO—, $NR^{16}$—CO—$C_{1-2}$alkyl-, —O—N=CH— or $C_{1-2}$alkyl;
$X^2$ represents a direct bond, O, —O—$C_{1-2}$alkyl-, CO, —CO—$C_{1-2}$alkyl-, $NR^{12}$, $NR^{12}$—$C_{1-2}$alkyl-, $NR^{17}$—CO—, $NR^{17}$—CO—$C_{1-2}$alkyl-, $Het^{20}$-$C_{1-2}$alkyl-, —O—N=CH— or $C_{1-2}$alkyl;
$R^1$ represents hydrogen, cyano, halo, hydroxy, formyl, $C_{1-6}$alkoxy-, $C_{1-6}$alkyl-, $C_{1-6}$alkoxy- substituted with halo,
  $C_{1-4}$alkyl substituted with one or where possible two or more substituents selected from hydroxy or halo;
$R^2$ represents hydrogen, cyano, halo, hydroxy, hydroxycarbonyl-, $Het^{16}$-carbonyl-, $C_{1-4}$alkyloxycarbonyl-, $C_{1-4}$alkylcarbonyl-, aminocarbonyl-, mono- or di($C_{1-4}$alkyl)aminocarbonyl-, $Het^1$, formyl, $C_{1-4}$alkyl-, $C_{2-6}$alkynyl-, $C_{3-6}$cycloalkyl-, $C_{3-6}$cycloalkyloxy-, $C_{1-6}$alkoxy-, $Ar^5$, $Ar^1$-oxy-, dihydroxyborane,
  $C_{1-6}$alkoxy- substituted with halo,
  $C_{1-4}$alkyl substituted with one or where possible two or more substituents selected from halo, hydroxy or $NR^5R^6$,
  $C_{1-4}$alkylcarbonyl- wherein said $C_{1-4}$alkyl is optionally substituted with one or where possible two or more substituents selected from hydroxy or $C_{1-4}$alkyl-oxy-;
$R^3$ represents hydrogen, $C_{1-4}$alkyl, cyano or $C_{1-4}$alkyl substituted with one or more substituents selected from halo, $C_{1-4}$alkyloxy-, amino-, mono- or di($C_{1-4}$alkyl)amino-, $C_{1-4}$alkyl-sulfonyl- or phenyl;
$R^4$ represents hydrogen, hydroxy, $Ar^3$-oxy, $Ar^4$-$C_{1-4}$alkyloxy-, $C_{2-4}$alkenyloxy- optionally substituted with $Het^{12}$ or $R^4$ represents $C_{1-4}$alkyloxy substituted with one or where possible two or more substituents selected from $C_{1-4}$alkyloxy-, hydroxy, halo, $Het^2$-, —$NR^7R^8$,-carbonyl- $NR^9R^{10}$ or $Het^3$-carbonyl-;
$R^5$ and $R^6$ are each independently selected from hydrogen or $C_{1-4}$alkyl;
$R^7$ and $R^8$ are each independently selected from hydrogen, $C_{1-4}$alkyl, $Het^8$, aminosulfonyl-, mono- or di ($C_{1-4}$alkyl)-aminosulfonyl, hydroxy-$C_{1-4}$alkyl-, $C_{1-4}$alkyl-oxy-$C_{1-4}$alkyl-, hydroxycarbonyl-$C_{1-4}$alkyl-, $C_{3-6}$cycloalkyl, $Het^9$-carbonyl-$C_{1-4}$alkyl-, $Het^{10}$-carbonyl-, polyhydroxy-$C_{1-4}$alkyl-, $Het^{11}$-$C_{1-4}$alkyl- or $Ar^2$—$C_{1-4}$alkyl-;
$R^9$ and $R^{10}$ are each independently selected from hydrogen, $C_{1-4}$alkyl, $C_{3-6}$cycloalkyl, $Het^4$, hydroxy-$C_{1-4}$alkyl-, $C_{1-4}$alkyloxy$C_{1-4}$alkyl- or polyhydroxy-$C_{1-4}$alkyl-;
$R^{11}$ represents hydrogen, $C_{1-4}$alkyl, $Het^5$, $Het^6$-$C_{1-4}$alkyl-, $C_{2-4}$alkenylcarbonyl- optionally substituted with $Het^7$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;
$R^{12}$ represents hydrogen, $C_{1-4}$alkyl, $C_{1-4}$alkyl-oxy-carbonyl-, $Het^{17}$, $Het^{18}$-$C_{1-4}$alkyl-, $C_{2-4}$alkenylcarbonyl- optionally substituted with $Het^{19}$-$C_{1-4}$alkylaminocarbonyl-, $C_{2-4}$alkenylsulfonyl-, $C_{1-4}$alkyloxy$C_{1-4}$alkyl- or phenyl optionally substituted with one or where possible two or more substituents selected from hydrogen, hydroxy, amino or $C_{1-4}$alkyloxy-;

$R^{13}$ represents hydrogen, $C_{1-4}$alkyl, $Het^{13}$, $Het^{14}$-$C_{1-4}$alkyl- or phenyl optionally substituted with one or where possible two or more substituents selected from hydrogen, hydroxy, amino or $C_{1-4}$alkyloxy-;

$R^{14}$ and $R^{15}$ are each independently selected from hydrogen, $C_{1-4}$alkyl, $Het^{15}$-$C_{1-4}$alkyl- or $C_{1-4}$alkyloxy$C_{1-4}$alkyl-;

$R^{16}$ and $R^{17}$ are each independently selected from hydrogen, $C_{1-4}$alkyl, $Het^{21}$-$C_{1-4}$alkyl- or $C_{1-4}$alkyloxy$C_{1-4}$alkyl-;

$Het^1$ represents a heterocycle selected from piperidinyl, morpholinyl, piperazinyl, furanyl, pyrazolyl, dioxolanyl, thiazolyl, oxazolyl, imidazolyl, isoxazolyl, oxadiazolyl, pyridinyl or pyrrolidinyl wherein said $Het^1$ is optionally substituted with one or where possible two or more substituents selected from amino, $C_{1-4}$alkyl, hydroxy-$C_{1-4}$alkyl-, phenyl, phenyl-$C_{1-4}$alkyl-, $C_{1-4}$alkyl-oxy-$C_{1-4}$alkyl- mono- or di($C_{1-4}$alkyl)amino- or amino-carbonyl-;

$Het^2$ represents a heterocycle selected from morpholinyl, piperazinyl, piperidinyl, pyrrolidinyl, thiomorpholinyl or dithianyl wherein said $Het^2$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl-, hydroxy-$C_{1-4}$alkyl-oxy-$C_{1-4}$alkyl-, mono- or di($C_{1-4}$alkyl)amino-, mono- or di($C_{1-4}$alkyl)amino-$C_{1-4}$alkyl-, amino$C_{1-4}$alkyl-, mono- or di($C_{1-4}$alkyl)amino-sulfonyl-, aminosulfonyl-;

$Het^3$, $Het^4$ and $Het^8$ each independently represent a heterocycle selected from morpholinyl, piperazinyl, piperidinyl, furanyl, pyrazolyl, dioxolanyl, thiazolyl, oxazolyl, imidazolyl, isoxazolyl, oxadiazolyl, pyridinyl or pyrrolidinyl wherein said $Het^3$, $Het^4$ or $Het^8$ is optionally substituted with one or where possible two or more substituents selected from hydroxy-, amino-, $C_{1-4}$alkyl-, $C_{3-6}$cycloalkyl-$C_{1-4}$alkyl-, aminosulfonyl-, mono- or di($C_{1-4}$alkyl)aminosulfonyl or amino-$C_{1-4}$alkyl-;

$Het^5$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^6$ and $Het^7$ each independently represent a heterocycle selected from morpholinyl, pyrrolidinyl, piperazinyl or piperidinyl wherein said $Het^6$ and $Het^7$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^9$ and $Het^{10}$ each independently represent a heterocycle selected from furanyl, piperidinyl, morpholinyl, piperazinyl, pyrazolyl, dioxolanyl, thiazolyl, oxazolyl, imidazolyl, isoxazolyl, oxadiazolyl, pyridinyl or pyrrolidinyl wherein said $Het^9$ or $Het^{10}$ is optionally substituted $C_{1-4}$alkyl, $C_{3-6}$cycloalkyl-$C_{1-4}$alkyl- or amino-$C_{1-4}$alkyl-;

$Het^{11}$ represents a heterocycle selected from indolyl or

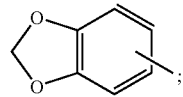

$Het^{12}$ represents a heterocycle selected from morpholinyl, piperazinyl, piperidinyl, pyrrolidinyl, thiomorpholinyl or dithianyl wherein said $Het^{12}$ is optionally substituted with one or where possible two or more substituents selected from hydroxy, halo, amino, $C_{1-4}$alkyl-, hydroxy-$C_{1-4}$alkyl-, $C_{1-4}$alkyl-oxy-$C_{1-4}$alkyl, hydroxy-$C_{1-4}$alkyl-oxy-$C_{1-4}$alkyl-, mono- or di($C_{1-4}$alkyl)amino- or mono- or di($C_{1-4}$alkyl)amino-$C_{1-4}$alkyl-;

$Het^{13}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alllkyl-, $C_{1-4}$alkyloxy$C_{1-4}$alkyl or polyhydroxy-$C_{1-4}$alkyl-;

$Het^{14}$ represent a heterocycle selected from morpholinyl, pyrrolidinyl, piperazinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{15}$ and $Het^{21}$ each independently represent a heterocycle selected from morpholinyl, pyrrolidinyl, piperazinyl or piperidinyl wherein said $Het^{15}$ or $Het^{21}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{16}$ represent a heterocycle selected from morpholinyl, pyrrolidinyl, piperazinyl, 1,3,2-dioxaborolane or piperidinyl wherein said heterocycle is optionally substituted with one or more substituents selected from $C_{1-4}$alkyl;

$Het^{17}$ represent a heterocycle selected from pyrrolidinyl or piperidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{18}$ and $Het^{19}$ each independently represent a heterocycle selected from morpholinyl, pyrrolidinyl, piperazinyl or piperidinyl wherein said $Het^{18}$ and $Het^{19}$ are optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-;

$Het^{20}$ represents a heterocycle selected from pyrrolidinyl, 2-pyrrolidinyl, piperidinyl, piperazinyl or pyrazolidinyl wherein said heterocycle is optionally substituted with one or where possible two or more substituents selected from $C_{1-4}$alkyl, $C_{3-6}$cycloalkyl, hydroxy-$C_{1-4}$alkyl-, $C_{1-4}$alkyloxy$C_{1-4}$alkyl or polyhydroxy-$C_{1-4}$alkyl-; and $Ar^1$, $Ar^2$, $Ar^3$, $Ar^4$ and $Ar^5$ each independently represent phenyl optionally substituted with cyano, $C_{1-4}$alkylsulfonyl-, $C_{1-4}$alkylsulfonylamino-, aminosulfonylamino-, hydroxy-$C_{1-4}$alkyl, aminosulfonyl-, hydroxy-, $C_{1-4}$alkyloxy- or $C_{1-4}$alkyl, said process, comprising;

a) coupling 2-acetoxy-8-chloropyrimido[5,4-d]pyrimidine derivatives (II) anilines of formula (III), to furnish the intermediates of formula (IV), and deprotecting the intermediates of formula (IV) followed by ring closure in the presence of a coupling reagent selected from the group consisting of 1,3-dicyclohexylcarbodiimide (DCC), N,N'-carbonyldiimidazole (CDI), POCl3, TiCl4, sulfur chloride fluoride (SO2ClF) or 1-(3-dimethylaminopropyl)-3-ethylcarbodiimide (EDCI), wherein V is a protective group selected from the group consisting of methylcarbonyl, t-butyl, methyl, ethyl, benzyl or trialkylsilyl;

formula (XXI), yielding the intermediate compounds of formula (XXII), followed by animating the pyrido[3,2-d]pyrimidine of formula (XXII) using an aminated alcohol (XXIII) that is added dropwise to a mixture of (XXII) in CH2Cl2 in the presence of 1,1'carbonylbis-1H-imidazole, followed by ring closure under Mitsunobu conditions to give the target compounds of formula (I")

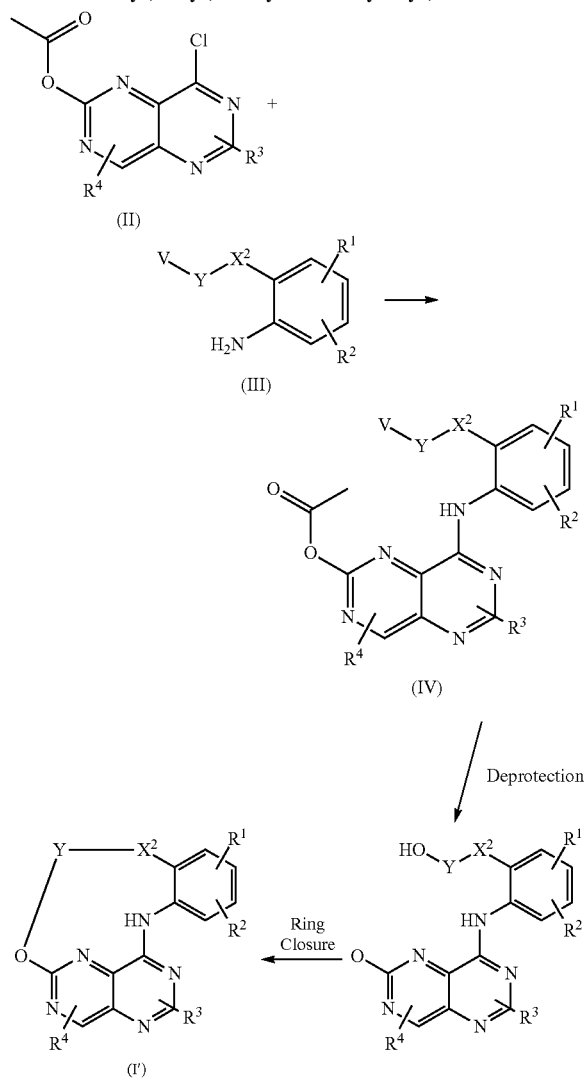

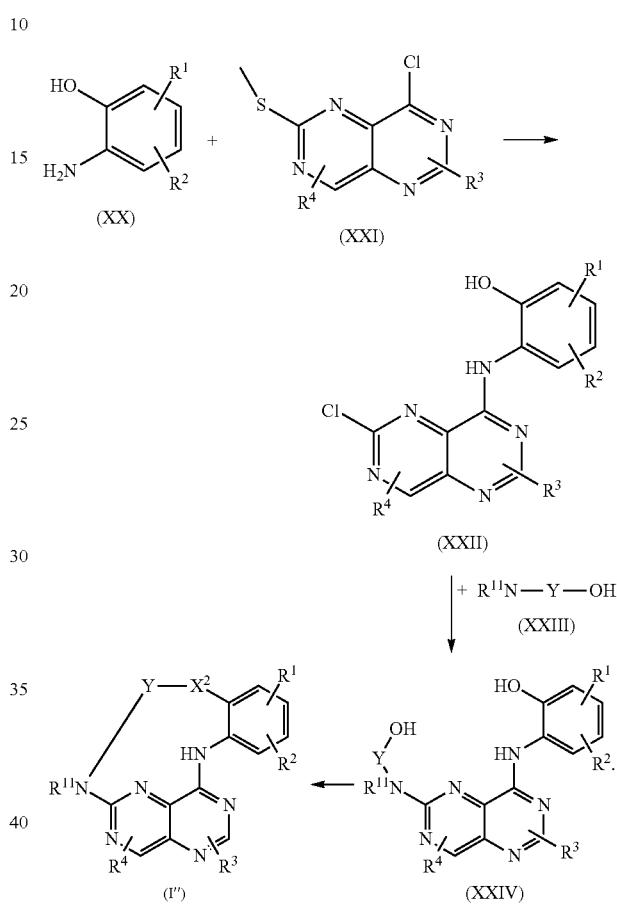

;or
b) coupling the known 8-chloro-2(methylthio)-pyrimido[5,4-d]pyrimidine with 2-aminophenol derivatives of 3. A method of treating ovarian cancer, the method comprising administering to an animal in need of such treatment a therapeutically effective amount of a compound as claimed in claim 1.

* * * * *